(12) United States Patent
Kimura

(10) Patent No.: US 8,228,063 B2
(45) Date of Patent: Jul. 24, 2012

(54) MAGNETIC RESONANCE IMAGING APPARATUS AND MAGNETIC RESONANCE IMAGING METHOD

(75) Inventor: Tokunori Kimura, Yaita (JP)

(73) Assignees: Kabushiki Kaisha Toshiba, Minato-Ku, Tokyo (JP); Toshiba Medical Systems Corporation, Otawara-Shi, Tochigi-Ken (JP)

( * ) Notice: Subject to any disclaimer, the term of this patent is extended or adjusted under 35 U.S.C. 154(b) by 413 days.

(21) Appl. No.: 12/503,161

(22) Filed: Jul. 15, 2009

(65) Prior Publication Data

US 2010/0013475 A1 Jan. 21, 2010

(30) Foreign Application Priority Data

Jul. 17, 2008 (JP) ................................ 2008-185829

(51) Int. Cl.
*G01V 3/00* (2006.01)
(52) U.S. Cl. ...................................... 324/309; 324/307
(58) Field of Classification Search .................. 324/309, 324/307, 310, 312
See application file for complete search history.

(56) References Cited

U.S. PATENT DOCUMENTS

| | | | | |
|---|---|---|---|---|
| 4,767,991 A | * | 8/1988 | Rzedzian | 324/312 |
| 5,332,968 A | * | 7/1994 | Brown | 324/309 |
| 6,888,350 B2 | | 5/2005 | Deimling | |
| 7,002,345 B2 | * | 2/2006 | Jara | 324/310 |
| 7,095,229 B2 | * | 8/2006 | Lorenz | 324/309 |
| 7,649,354 B2 | * | 1/2010 | Bayram et al. | 324/309 |
| 7,902,823 B2 | * | 3/2011 | Griswold et al. | 324/307 |
| 8,032,201 B2 | * | 10/2011 | Taniguchi et al. | 600/410 |

FOREIGN PATENT DOCUMENTS

| | | |
|---|---|---|
| CN | 1418597 A | 11/2002 |
| JP | 2002-253526 | 9/2002 |
| WO | WO 99/14616 | 3/1999 |

OTHER PUBLICATIONS

Bernstein et al., "Handbook of MRI Pulse Sequence", *Elsevier Academic Press*, (No Date), pp. 379-393.
Chinese office action dated Dec. 24, 2010, issued in CN 200910160417.3.

* cited by examiner

*Primary Examiner* — Louis Arana
(74) *Attorney, Agent, or Firm* — Nixon & Vanderhye PC

(57) ABSTRACT

A magnetic resonance imaging apparatus includes a data acquisition unit and an image data generating unit. The data acquisition unit acquires plural pieces of magnetic resonance data for generating plural species of image data of which contrasts are mutually different from a same object with mutually different data amounts by setting parameters for controlling the contrasts to mutually different values. The image data generating unit generates the plural species of the image data by image reconstruction processing and composition processing of the plural pieces of the magnetic resonance data or plural pieces of data derived from the plural pieces of the magnetic resonance data.

24 Claims, 17 Drawing Sheets

(A) $b_0$ (b=0) DATA (B) $b_n$ (b>0) DATA

MAGNETIC RESONANCE IMAGING APPARATUS AND MAGNETIC RESONANCE IMAGING METHOD

BACKGROUND OF THE INVENTION

1. Field of the Invention

The present invention relates to a MRI (magnetic resonance imaging) apparatus and a magnetic resonance imaging method which excite nuclear spin of an object magnetically with a RF (radio frequency) signal having the Larmor frequency and reconstruct an image based on NMR (nuclear magnetic resonance) signals generated due to the excitation, and more particularly, to a magnetic resonance imaging apparatus and a magnetic resonance imaging method which acquire plural images corresponding to mutually different parameters such as TRs and/or TEs with regard to a same object.

2. Description of the Related Art

Magnetic Resonance Imaging is an imaging method which excites nuclear spin of an object set in a static magnetic field with a RF signal having the Larmor frequency magnetically and reconstruct an image based on NMR signals generated due to the excitation.

In magnetic resonance imaging, various species of parameter image such as a longitudinal relaxation (T1) weighted image (T1WI), a transverse relaxation (T2) weighted image (T2WI), a proton density weighted image (PDWI), a FLAIR (fluid attenuated IR) image, a diffusion weighted image (DWI) or a perfusion weighted image (PWI) of blood flow in a capillary vessel is imaged by changing a parameter serving as an imaging condition such as a repetition time (TR), an echo time (TE), an inversion time (TI) in case of a scan under an inversion recovery (IR) method, a b-factor indicating an intensity of a MPG (motion probing gradient) pulse applied in a diffusion weighted imaging (DWI), an application and an intensity of a pre-pulse to control a contrast.

FIG. 1 is a chart showing an example of pulse sequence for acquiring a DWI and a non-DWI of a same object in the conventional MRI apparatus.

In each of (A) and (B) of FIG. 1, ECHO, Gr and Ge denote echo data (magnetic resonance signals) to be acquired, gradient magnetic fields for RO (readout) and gradient magnetic fields for PE (phase encode).

As shown in FIG. 1, respective scans are performed according to two different sequences (A) and (B) in case of acquiring a DWI and non-DWI from a same object.

That is, in case of acquiring a DWI as shown in FIG. 1 (A), echo data is acquired according to an EPI (echo planar imaging) sequence with application of a MPG pulse by setting a b-factor to bn which is non-zero, for example. More specifically, Nr echo signals are respectively acquired with a sampling pitch Δt, and an echo signal train consisting of the Nr echo signals is acquired at an echo train spacing (ETS) Ne/m times per single shot. Then, Ne echo signal trains are acquired by m shots of data acquisition.

In contrast, in case of acquiring a non-DWI as shown in FIG. 1 (B), echo data is acquired by an EPI sequence without application of a MPG pulse, i.e., with setting a b-factor to b0 which can be regarded as zero, as with DWI acquisition.

FIG. 2 is a diagram showing a method for arranging the echo data, acquired by the pulse sequence shown in FIG. 1, in k-space (Fourier space).

In each of (A) and (B) of FIG. 2, the abscissa axis denotes the readout direction Kr in k-space and the ordinate axis denotes phase encode direction Ke in k-space. As shown in FIG. 2, echo data (bn data) acquired by the DWI sequence with b=bn and echo data (b0 data) acquired by the non-DWI sequence with b=b0 are arranged in individual k-spaces respectively. In the case where the number of shots m=3 for example, Ne/3 echo signal trains are acquired three times, and the number of data in a phase encode direction becomes Ne. Since a single echo signal train consists of Nr echo signals, the number of data in a readout direction becomes Nr.

In such magnetic resonance imaging, techniques to shorten an imaging time include the echo train imaging that acquires k-space data separately. The echo train imaging acquires multiple echo signals corresponding to mutually different TEs with changing a phase encode after a single excitation by a FSE (fast spin echo) sequence or an EPI sequence, and arranges the echo signals corresponding to the mutually different TEs on corresponding frequencies in k-space to acquire an image.

Further, techniques to improve a time resolution include a technique called keyhole. The keyhole is frequently used in a dynamic imaging using contrast medium (see, for example, "Glossary of Clinical Magnetic Resonance Imaging", page 107 and page 333, Chief Editor: Kazuhiro Tsuchiya, Editor: Kazuyuki Ohgi, Medical View Co., Ltd). Specifically, while data is acquired over entire frequency band before injection of contrast medium, data in only a low frequency region is acquired after the injection of the contrast medium and the data acquired before the injection of the contrast medium is used for data in a high frequency region or the time resolution in the high frequency region is reduced. Consequently, the time resolution can be improved without reducing the spatial resolution or a width of FOV (field of view).

However, in a MRI apparatus, various images of a same object are imaged such as a T1WI, a T2WI, a PDWI, a FLAIR image, a DWI and a PWI with mutually different parameters including a TR and a TE. Since it is necessary that the number of multiple images equivalent to the number of different parameters are separately acquired, there is a problem that an imaging time is long in a MRI apparatus compared to an image diagnostic apparatus such as an X-ray CT (computed tomography) apparatus.

SUMMARY OF THE INVENTION

The present invention has been made in light of the conventional situations, and it is an object of the present invention to provide a magnetic resonance imaging apparatus and a magnetic resonance imaging method which make it possible to acquire plural images corresponding to mutually different parameters such as TRs and/or TEs with regard to a same object in a shorter time.

The present invention provides a magnetic resonance imaging apparatus comprising: a data acquisition unit configured to acquire plural pieces of magnetic resonance data for generating plural species of image data of which contrasts are mutually different from a same object with mutually different data amounts by setting parameters for controlling the contrasts to mutually different values; and an image data generating unit configured to generate the plural species of the image data by image reconstruction processing and composition processing of the plural pieces of the magnetic resonance data or plural pieces of data derived from the plural pieces of the magnetic resonance data, in an aspect to achieve the object.

The present invention also provides a magnetic resonance imaging method comprising: acquiring plural pieces of magnetic resonance data for generating plural species of image data of which contrasts are mutually different from a same object with mutually different data amounts by setting parameters for controlling the contrasts to mutually different values; and generating the plural species of the image data by image reconstruction processing and composition processing of the plural pieces of the magnetic resonance data or plural pieces of data derived from the plural pieces of the magnetic resonance data, in an aspect to achieve the object.

The magnetic resonance imaging apparatus and the magnetic resonance imaging method according to the present invention as described above make it possible to acquire plural images corresponding to mutually different parameters such as TRs and/or TEs with regard to a same object in a shorter time.

DESCRIPTION OF THE PREFERRED EMBODIMENTS

A magnetic resonance imaging apparatus and a magnetic resonance imaging method according to embodiments of the present invention will be described with reference to the accompanying drawings.

(Configuration and Function)

Figure 3:
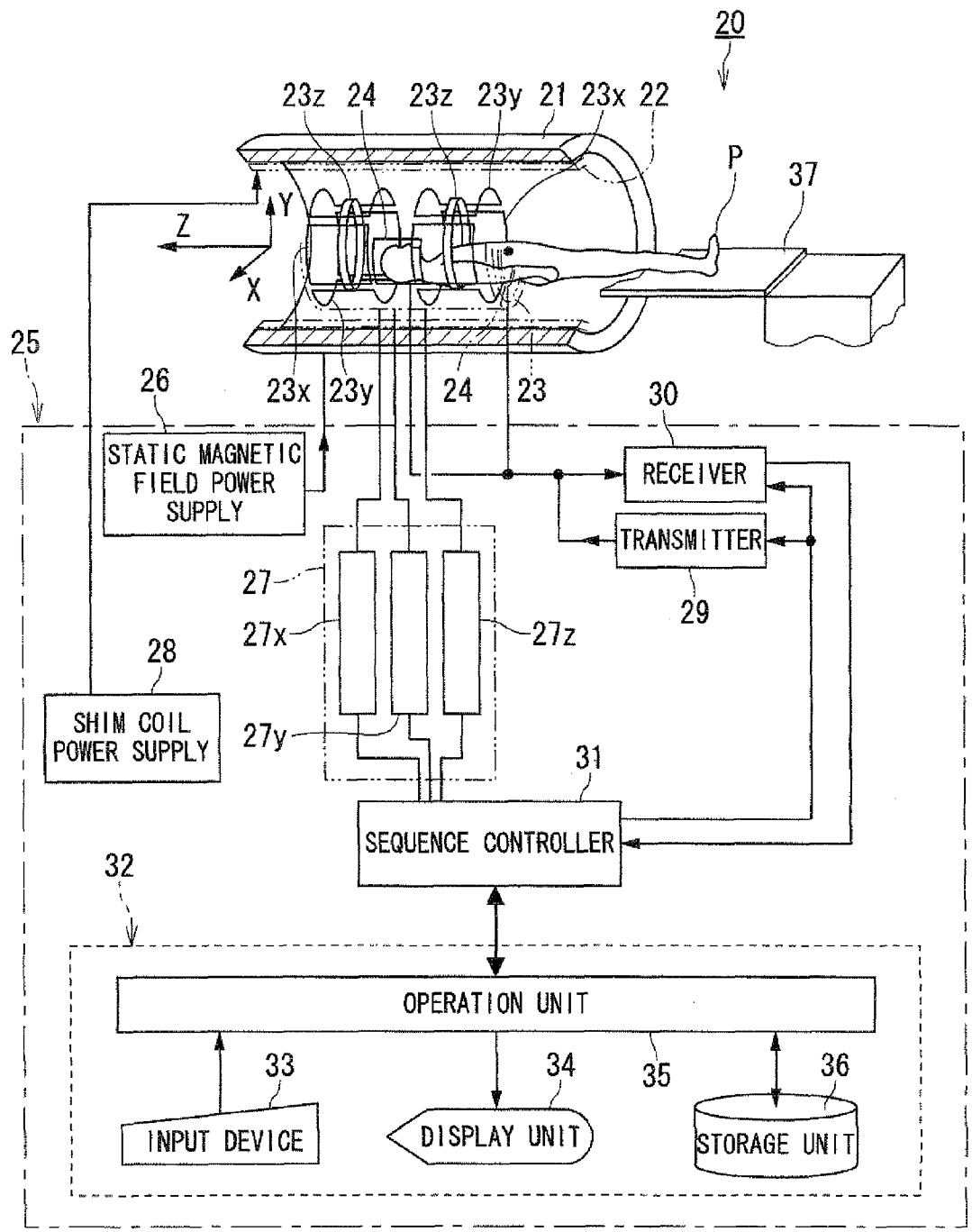
FIG. 3 is a block diagram showing a magnetic resonance imaging apparatus according to an embodiment of the present invention.

FIG. 3 is a block diagram showing a magnetic resonance imaging apparatus according to an embodiment of the present invention.

A magnetic resonance imaging apparatus 20 includes a static field magnet 21 for generating a static magnetic field, a shim coil 22 arranged inside the static field magnet 21 which is cylinder-shaped, a gradient coil 23 and RF coils 24.

The magnetic resonance imaging apparatus 20 also includes a control system 25. The control system 25 includes a static magnetic field power supply 26, a gradient power supply 27, a shim coil power supply 28, a transmitter 29, a receiver 30, a sequence controller 31 and a computer 32. The gradient power supply 27 of the control system 25 includes an X-axis gradient power supply 27x, a Y-axis gradient power supply 27y and a Z-axis gradient power supply 27z. The computer 32 includes an input device 33, a display unit 34, an operation unit 35 and a storage unit 36.

The static field magnet 21 communicates with the static magnetic field power supply 26. The static magnetic field power supply 26 supplies electric current to the static field magnet 21 to get the function to generate a static magnetic field in an imaging region. The static field magnet 21 includes a superconductivity coil in many cases. The static field magnet 21 gets current from the static magnetic field power supply 26 which communicates with the static field magnet 21 at excitation. However, once excitation has been made, the static field magnet 21 is usually isolated from the static magnetic field power supply 26. The static field magnet 21 may include a permanent magnet which makes the static magnetic field power supply 26 unnecessary.

The static field magnet 21 has the cylinder-shaped shim coil 22 coaxially inside itself. The shim coil 22 communicates with the shim coil power supply 28. The shim coil power supply 28 supplies current to the shim coil 22 so that the static magnetic field becomes uniform.

The gradient coil 23 includes an X-axis gradient coil 23x, a Y-axis gradient coil 23y and a Z-axis gradient coil 23z. Each of the X-axis gradient coil 23x, the Y-axis gradient coil 23y and the Z-axis gradient coil 23z which is cylinder-shaped is arranged inside the static field magnet 21. The gradient coil 23 has also a bed 37 in the area formed inside it which is an imaging area. The bed 37 supports an object P. The RF coils 24 include a whole body coil (WBC: whole body coil), which is built in the gantry, for transmission and reception of RF signals and local coils, which are arranged around the bed 37 or the object P, for reception of RF signals.

The gradient coil 23 communicates with the gradient power supply 27. The X-axis gradient coil 23x, the Y-axis gradient coil 23y and the Z-axis gradient coil 23z of the gradient coil 23 communicate with the X-axis gradient power supply 27x, the Y-axis gradient power supply 27y and the Z-axis gradient power supply 27z of the gradient power supply 27 respectively.

The X-axis gradient power supply 27x, the Y-axis gradient power supply 27y and the Z-axis gradient power supply 27z supply currents to the X-axis gradient coil 23x, the Y-axis gradient coil 23y and the Z-axis gradient coil 23z respectively so as to generate gradient magnetic fields Gx, Gy and Sz in the X, Y and Z directions in the imaging area.

The RF coils 24 communicate with the transmitter 29 and/or the receiver 30. The transmission RF coil 24 has a function to transmit a RF signal given from the transmitter 29 to the object P. The reception RF coil 24 has a function to receive a MR signal generated due to an nuclear spin inside the object P which is excited by the RF signal to give to the receiver 30.

Figure 1:
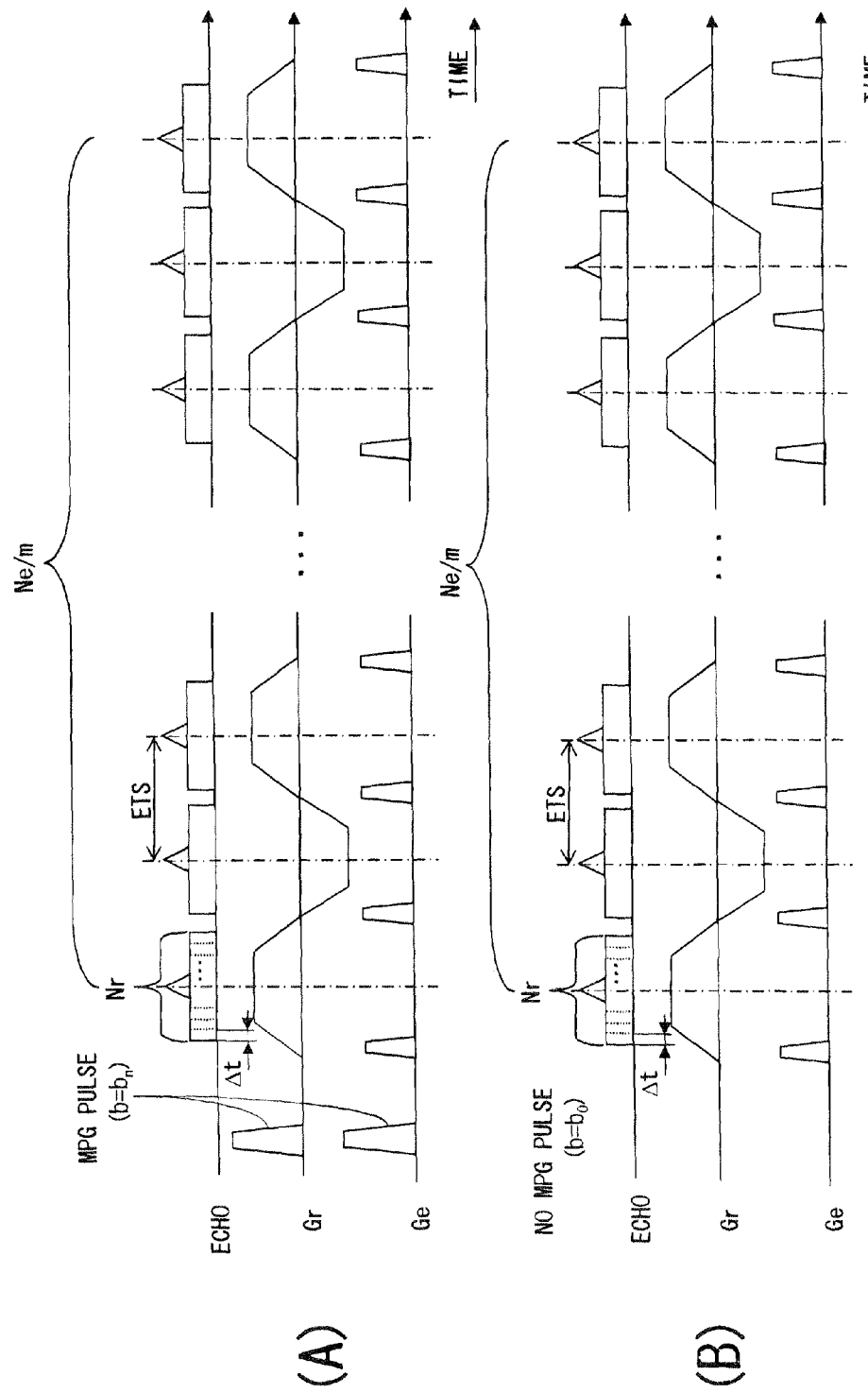
FIG. 1 is a chart showing an example of pulse sequence for acquiring a DWI and a non-DWI of a same object in the conventional MRI apparatus.
Figure 2:
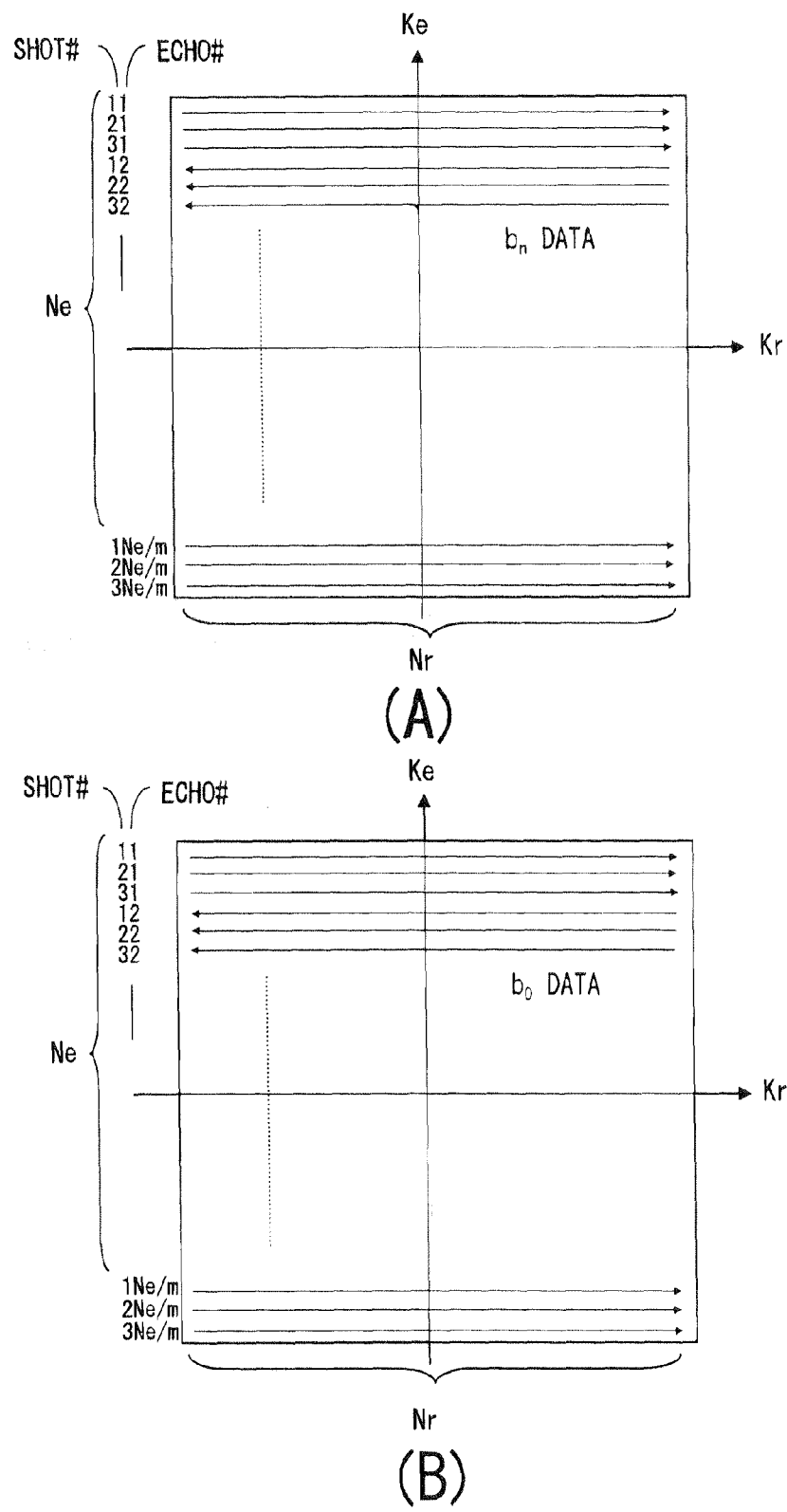
FIG. 2 is a diagram showing a method for arranging the echo data, acquired by the pulse sequence shown in FIG. 1, in k-space (Fourier space)
Figure 4:
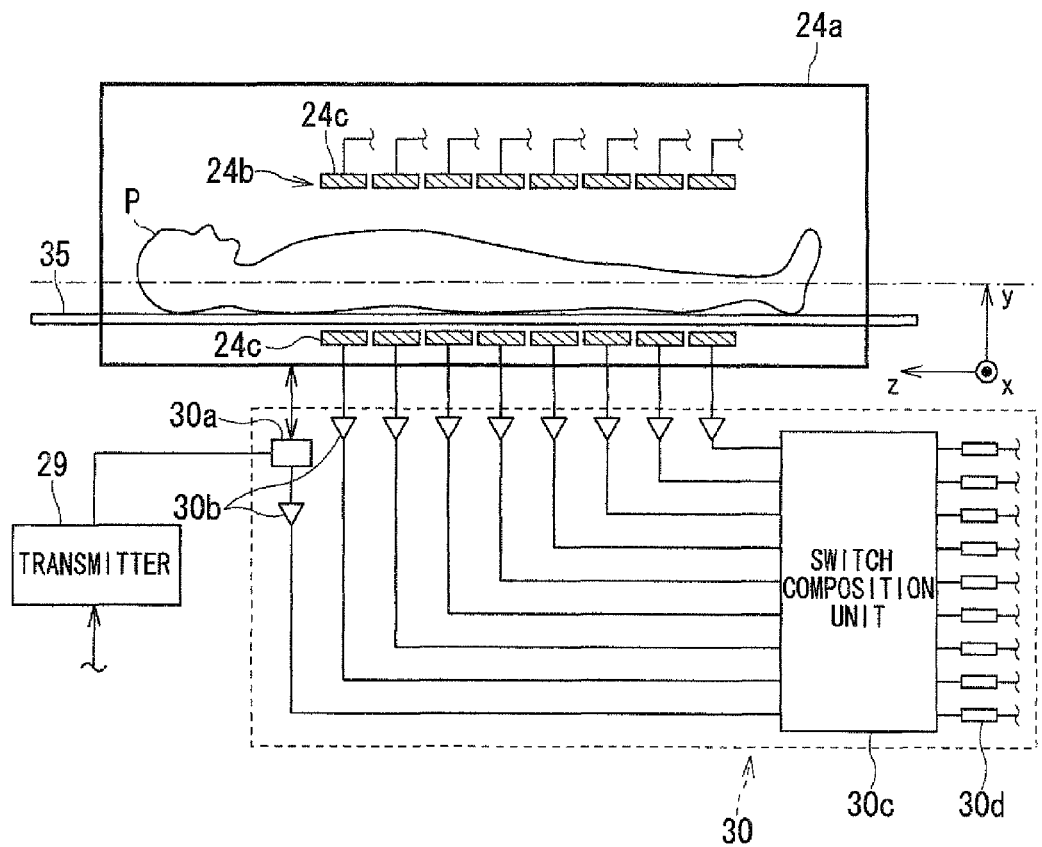
FIG. 4 is a diagram showing an example of detail structure of the RF coils shown in FIG. 1.
Figure 5:
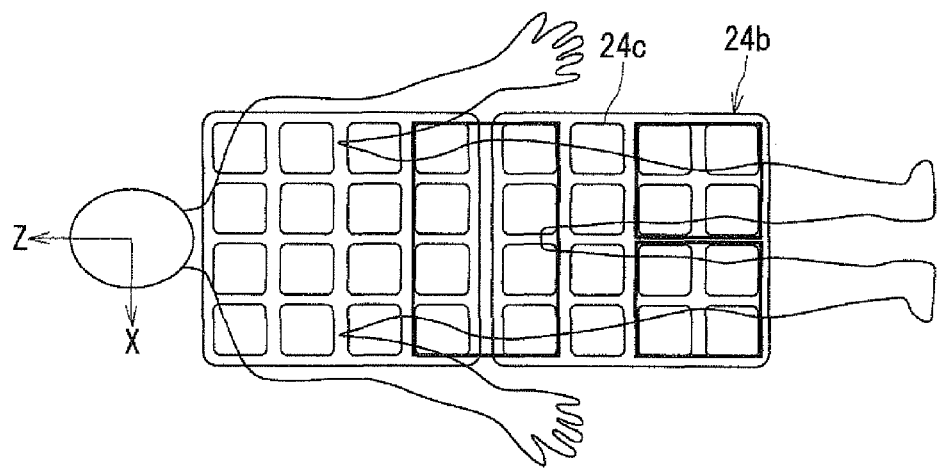
FIG. 5 is a diagram showing an example arrangement of the coil elements set on the body surface side of the object shown in FIG. 4.
Figure 6:
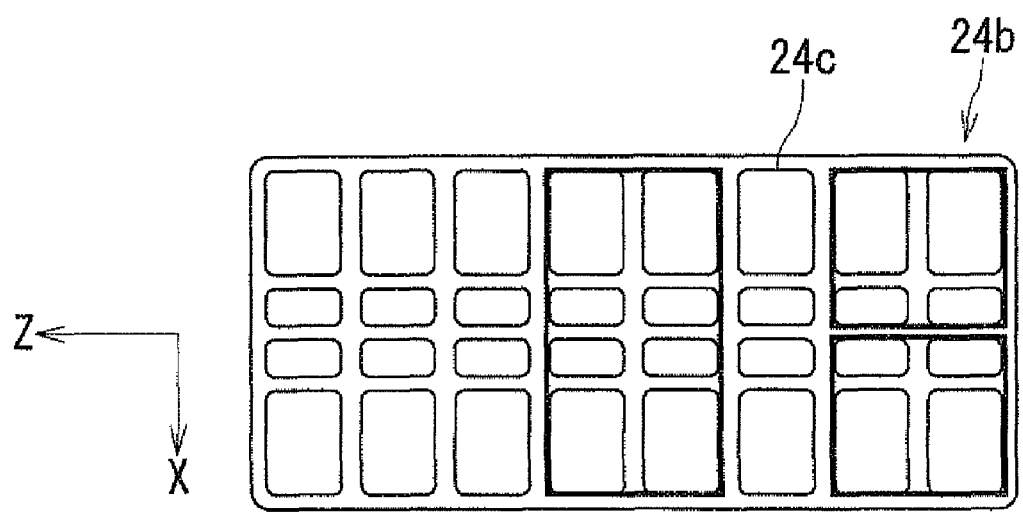
FIG. 6 is a diagram showing an example arrangement of the coil elements set on the back surface side of the object shown in FIG. 4.

FIG. 4 is a diagram showing an example of detail structure of the RF coils 24 shown in FIG. 1. FIG. 5 is a diagram showing an example arrangement of the coil elements 24c set on the body surface side of the object P shown in FIG. 4. FIG. 6 is a diagram showing an example arrangement of the coil elements 24c set on the back surface side of the object P shown in FIG. 4.

As shown in FIG. 4, the RF coils 24 include a cylindrical WB (whole-body) coil 24a, and a phased array coil 24b. The phased array coil 24b includes a plurality of coil elements 24c, and a plurality of the coil elements 24c is arranged on each of the body surface side and the back surface side of the object P.

For example, as shown in FIG. 5, on the body surface side of the object P, four rows of coil elements 24c are provided in the x-direction and eight columns of them in the z-direction, that is, a total of thirty two coil elements 24c are arranged so as to cover a wide-ranging imaging area. Likewise, as shown in FIG. 6, on the back surface side of the object, four rows of coil elements 24c are provided in the x-direction and eight columns of them in the z-direction, that is, a total of thirty two coil elements 24c are arranged so as to cover a wide-ranging imaging area. On the back surface side, coil elements 24 with a smaller size than that of the other coil elements 24c are arranged in the vicinity of the body axis from the viewpoint of sensitivity improvement, considering for the presence of the backbone of the object P.

On the other hand, the receiver 30 includes a duplexer 30a, amplifiers 30b, a switch composition unit 30c, and reception circuits 30d. The duplexer 30a is connected to the transmitter 29, the WB coil 24a, and the amplifier 30b for the WB coil 24a. The amplifiers 30b are provided by the total number of the coil elements 24c and the WB coil 24a, and each connected to a respective one of the coil elements 24c and the WB coil 24a. The switch composition unit 30c consists of a single piece or a plurality of pieces. The input side of the switch composition unit 30c is connected to the plurality of coil element units 24c or the WB coil 24a through the plurality of amplifiers 30b. The reception circuits 30d are provided by a desired number such as to be smaller than or equal to the total number of the coil elements 24c and the WB coil 24a, and disposed on the output side of the switch composition unit 30c.

The WB coil 24a can be used as a coil for the transmission of RF signals. As a coil for the reception of NMR signals, each of the coil elements 24c can be used. Furthermore, the WB coil 24a can also be used for a receiving coil.

Therefore, the duplexer 30a is configured so as to provide the WB coil 24a with radio frequency signals for transmission, outputted from the transmitter 29, while providing the switch composition unit 30c with NMR signals received in the WB coil 24a via the amplifiers 30b in the receiver 30. An NMR signal received in each of the coil elements 24c is outputted to the switch composition unit 30c via a respective one of the amplifiers 30b.

The switch composition unit 30c is configured so as to perform composition processing and switching with respect to NMR signals received from the coil elements 24c or the WE coil 24a and to output them to the corresponding reception circuits 30d. In other words, the switch composition unit 30c is configured so that, in conformance with the number of the reception circuits 30d, the composition processing and switching with respect to NMR signals received from the coil elements 24c or the WB coil 24a are performed in the switch composition unit 30c, and that NMR signals can be received from various imaging areas by forming sensibility distributions in response to the imaging areas, using a plurality of desired coil elements 24c.

However, NMR signals may be received by WE coil 24a alone without providing the coil elements 24c. Also, NMR signals received in the coil elements 24c or the WB coil 24a may be directly outputted to the reception circuits 30d without providing the switch composition unit 30c. Furthermore, more coil elements 24c may be extensively arranged.

The sequence controller 31 of the control system 25 communicates with the gradient power supply 27, the transmitter 29 and the receiver 30. The sequence controller 31 has a function to storage sequence information describing control information needed in order to make the gradient power supply 27, the transmitter 29 and the receiver 30 drive and generate gradient magnetic fields Gx, Gy and Cz in the X, Y and Z directions and a RF signal by driving the gradient power supply 27, the transmitter 29 and the receiver 30 according to a predetermined sequence stored. The control information above-described includes motion control information, such as intensity, impression period and impression timing of the pulse electric current which should be impressed to the gradient power supply 27

The sequence controller 31 is also configured to give raw data to the computer 32. The raw data is complex data obtained through the detection of a NMR signal and A/D (analog to digital) conversion to the NMR signal detected in the receiver 30.

The transmitter 29 has a function to give a RF signal to the RF coil 24 in accordance with control information provided from the sequence controller 31. The receiver 30 has a function to generate raw data which is digitized complex number data by detecting a MR signal given from the RF coil 24 and performing predetermined signal processing and A/D converting to the MR signal detected. The receiver 30 also has a function to give the generated raw data to the sequence controller 31.

The computer 32 gets various functions by the operation unit 35 executing some programs stored in the storage unit 36 of the computer 32. Alternatively, some specific circuits having various functions may be provided with the magnetic resonance imaging apparatus 20 instead of using some of the programs.

Figure 7:
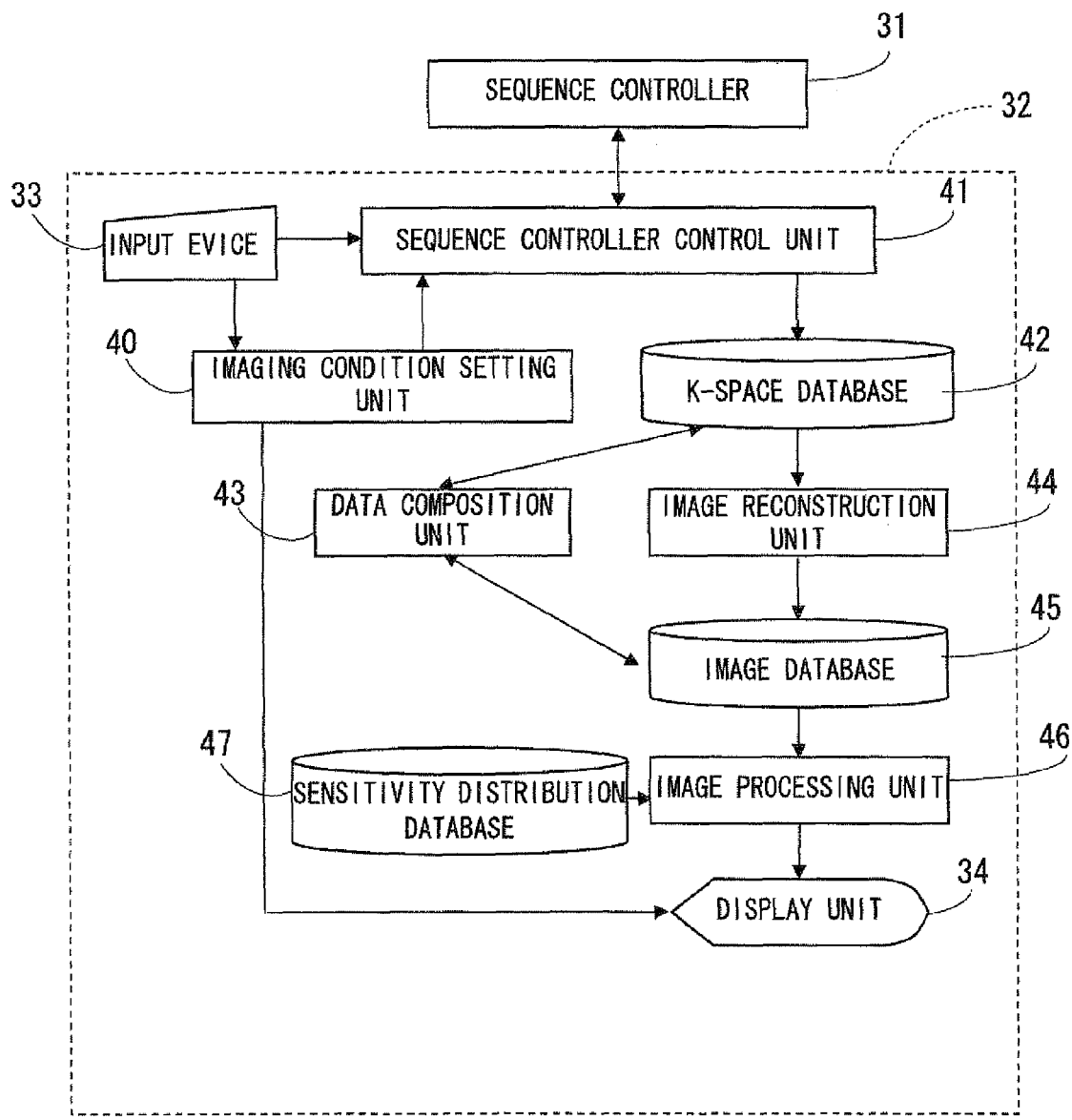
FIG. 7 is a functional block diagram of the computer shown in FIG. 3.

FIG. 7 is a functional block diagram of the computer 32 shown in FIG. 3.

The computer 32 functions as an imaging condition setting unit 40, a sequence controller control unit 41, a k-space database 42, a data composition unit 43, an image reconstruction unit 44, an image database 45, an image processing unit 46 and a sensitivity distribution database 47 by program.

The imaging condition setting unit 40 has a function to set an imaging condition including a pulse sequence based on instruction from the input device 33 and to provide the set imaging condition to the sequence controller control unit 41. For that purpose, the imaging condition setting unit 40 has a function to display screen information for setting imaging condition on the display unit 34.

In the imaging condition setting unit 40, an imaging condition for PI (parallel imaging) which is high speed imaging technology can be set. PI is an imaging method for reducing the number of the phase encodes necessary for image reconstruction by receiving echo data with plural coil elements 24c and skipping phase encodes. In principle, the number of the phase encodes can be reduced down to the number derived by dividing the number of the phase encodes necessary for image reconstruction by the number of coil elements 24c. A scan under an EPI method which acquires plural echo signals continuously is performed by PI in many cases. When PI is performed, information necessary for PI including the number of coil elements 24c for acquiring echo data, information associating each coil element 24c with an imaging part and a speed scale rate (speed-up factor) R is set as an imaging condition. The speed scale rate R is a rate of a data acquisition speed with PI to that without PI. Therefore, the speed scale rate R can be set up to a value of smaller one of the number of element coils 24c used for receiving data and the number of reception channels in theory.

The sequence controller control unit 41 has a function for controlling the driving of the sequence controller 31 by giving an imaging condition including a pulse sequence to the sequence controller 31 based on information from the input device 33 or another element. Further, the sequence controller control unit 41 has a function for receiving raw data from the sequence controller 31 and arranging the raw data to k space formed in the k-space database 42. Therefore, the raw data generated by the receiver 30 is stored as k space data in the k-space database 42.

Particularly, the above-mentioned imaging condition setting unit 40 has the function to set plural imaging conditions to acquire plural different species of parameter images respectively corresponding to mutually different parameters to control a contrast. The parameter image data can be not only 2D (two-dimensional) image data or 3D (three-dimensional) image data with arbitrary axes out of the special axes including the x-axis, y-axis and z-axis but dynamic image data with the time axis t. Therefore, an imaging condition to acquire 4D (four-dimensional) image data with four axes of (x, y, z, t) may be set.

However, a pulse sequence to acquire at least one parameter image is set to a full data acquisition sequence that acquires all data in k-space necessary to generate image data and a pulse sequence to acquire at least another parameter image is set to a partial data acquisition sequence that acquires only data in a partial region out of data in k-space necessary to generate image data. That is, plural (the first, the second, . . . , the N-th) pulse sequences with mutually different volumes of data to be acquired are set as imaging conditions.

Then, for data in a region without acquiring data for a certain parameter image, data for another parameter image of which data is acquired from all regions is used as a substitute as described hereinbelow. Consequently, the volume of data to be acquired is reduced depending on a volume of commonly used data in case of acquiring multiple different species of parameter images, and therefore, an imaging time can be totally shortened.

Parameters to control a contrast include a TR, a TE, a TI in a scan by the TR method, a b-factor representing an intensity of a MPG pulse applied in DWI, whether a pre-pulse to control a contrast is applied, and an intensity of a pre-pulse to control a contrast. The TR is a time from an excitation pulse to the next excitation pulse. The TE is a time from a center of an excitation pulse to a peak of an echo. The IR method is a method to invert a longitudinal magnetization component in the z-axis by applying a 180 degrees inversion pulse as a pre-pulse prior to applying a 90 degrees pulse, and to acquire FID (free induction decay) signals by applying a 90 degrees pulse or echo signals by a scan during the recovery of the longitudinal magnetization by the T1. The TI in the IR method is a time interval between the initial 180 degrees inversion pulse and the next 90 degrees pulse.

By performing an imaging by setting these parameter values to mutually different values, multiple various kinds of parameter images such as a T1WI, a T2WI, a PDWI, a FLAIR image, a DWI and/or a PWI having mutually different contrasts are acquired.

For example, when the TR is set to a shorter time than a T1 time of a tissue and the TE is set to a much shorter time than a T2 time in a scan by a SE (spin echo) method or a FE (field echo) method, a T1WI can be acquired with an emphasized difference in T1 between respective tissues and less influence of the T2. Also in the IR method, an image can be acquired with the T1 much weighted since a recovery velocity from an inversion state depends on only the T1. Then, the T1 weighted degree can be changed by adjusting the TI.

On the contrary, when the TR is set to a long time so that spins in all tissues recover, a difference in T1 among tissues is not reflected in an image. Moreover, when the TE is set to a long time, a T2WI where a difference in T2 among tissues is emphasized can be acquired.

Meanwhile, when the TR is set to a long time and the TE is set to a short time, a PDWI that is less affected by both the T1 and the T2 can be acquired. The PDWI reflects mainly a density of protons. The PDWI is often called the spin density image.

When the TI in the IR method is set to about 1500-2500 ms with which a magnetization of a CSF (cerebrospinal fluid) passes through the zero point, a FLAIR image with water signals such as signals from the CFS suppressed can be acquired.

When a MPG pulse that is a gradient magnetic field pulse having a high intensity is applied over a long time, a phase shift generated by a transfer of each magnetization vector during application of the MPG pulse becomes not negligible and a DWI having lower signal intensities in a region where diffusion is more active can be acquired. Note that, a DWI of blood flow in a capillary vessel is called a PWI and differentiated from an ordinary DWI. An index representing an intensity of a MPG pulse is the b-factor. Non-DWI data can be acquired with setting b☐0, and DWI data can be acquired with setting b>0. The b-factor is generally a tensor quantity, and is determined depending on a magnitude and an application direction of a MPG pulse. Therefore, an application direction of a MPG pulse is also a parameter to control a contrast.

Pre-pulses for controlling contrast include a selective excitation pulse such as a water selective excitation pulse, a suppression pulse such as a fat saturation pulse and a silicone suppression pulse, a spin labeling (also referred to tagging or labeling) pulse such as a SORS (slice-selective off-resonance sinc pulse), a t-SLIP (TIME-SLIP: time-Spatial Labeling Inversion Pulse) and an ASL (Arterial spin labeling) pulse, a MTC (magnetization transfer contrast) pulse and a saturation (Presat: presaturation) pulse.

The water selective excitation pulse is a pre-pulse to excite water selectively and the fat saturation pulse is a pre-pulse to suppress a fat. Some selective excitation pulses and suppression pulses such as a water selective excitation pulse and a fat saturation pulse use chemical shift that a resonant frequency is different from that of another matter. Examples of fat saturation pulses using chemical shift include a CHESS pulse.

The spin labeling pulse is a pre-pulse for tagging a moving object such as blood and cerebrospinal fluid (CSF) flowing into an imaging section. Especially, a spin labeling pulse for labeling spins of blood is called an ASL pulse. There is a t-SLIP with application of plural pulses for labeling as one of spin labeling pulses.

A t-SLIP is configured with a region non-selective inversion pulse and a region selective inversion pulse. A region non-selective inversion pulse can be witched into ON/OFF state. That is, a t-SLIP includes at least a region selective inversion pulse, and is configured with only a region selective inversion pulse, or alternatively, with both of a region selective inversion pulse and a region non-selective inversion pulse.

A region selective inversion pulse can be set arbitrarily independent of an imaging section. When blood flowing into an imaging region is labeled with a region selective inversion pulse, signal intensity at the part to which the blood reaches after a TI becomes high. Note that, when a region non-selective inversion pulse is set to OFF, signal intensity at the part to which the blood reaches after a TI becomes low. Therefore, a moving direction and a distance of blood can be recognized. That is, signal intensity of only blood which reaches to an imaging section after a TI can be enhanced or suppressed selectively.

A preset pulse is a pre-pulse for suppressing signals from a desired matter by saturating spins of the desired matter. A presat pulse is applied before an application of a dephasing gradient magnetic field. A MTC pulse is a pre-pulse for saturating a magnetization of absorbed water protons by using MTC effect to suppress signals from a parenchymatous organ. A SORS is a MTC pulse applied with a slice selective gradient magnetic field.

Meanwhile, a difference in frequency space distribution of data in k-space among different species of parameter images becomes generally larger in a lower frequency region, and smaller in a higher frequency region. Therefore, it is often the case that pieces of data in k-spaces corresponding to different species of parameter images are regard as equal in a high frequency region and data can be shared. In additions a fewer scans to acquire all data in k-space, that is, a single scan, will lead to shortening of an imaging time. For that reason, hereinafter it will be described that a full data acquisition sequence for acquiring all data in k-space is set for one representative parameter image, a partial data acquisition sequence for acquiring data in only a low frequency region in k-space is set for the other single parameter image or each of the other multiple parameter images and data is shared in a high frequency region in the k-spaces corresponding to the multiple different species of parameter images.

Figure 8:
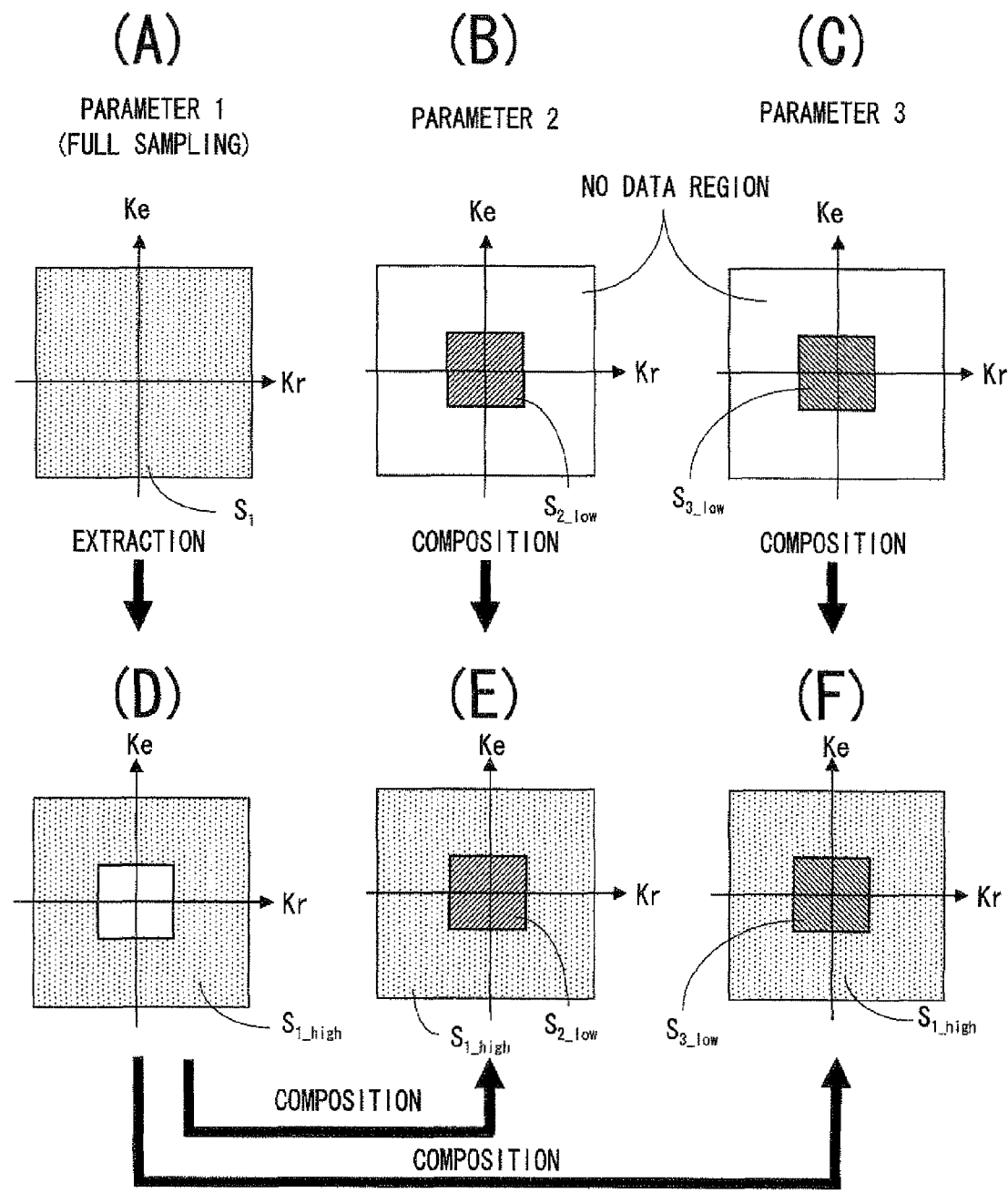
FIG. 8 is a diagram showing an example of ranges of pieces of k-space data acquired by three pulse sequences set in the imaging condition setting unit shown in FIG. 7 and a composition method of the acquired pieces of k-space data.

FIG. 8 is a diagram showing an example of ranges of pieces of k-space data acquired by three pulse sequences set in the imaging condition setting unit 40 shown in FIG. 7 and a composition method of the acquired pieces of k-space data.

In each ordinate axis and abscissa axis of FIG. 8 denote phase encode direction Ke and readout direction Kr respectively in k-space. As shown in FIG. 8 (A), k-space data S1 for generating an image corresponding to a parameter 1 is acquired over the entire frequency region by an arbitrary full data acquisition sequence. Meanwhile, as shown in (B) and (C) of FIG. 8 respectively, k-space data $S2_{low}$ for generating an image corresponding to a parameter 2 that is different from the parameter 1 and k-space data $S3_{low}$, for generating an image corresponding to a parameter 3 that is different from the parameter 1 and the parameter 2 are acquired with regard to only a low frequency region by arbitrary partial data acquisition sequences respectively.

The acquired k-space data S1 for generating the image corresponding to the parameter 1, k-space data $S2_{low}$ for generating the image corresponding to the parameter 2 and k-space data $S3_{low}$ for generating the image corresponding to the parameter 3 are stored in the k-space database 42 and arranged in the corresponding k-spaces respectively.

Consequently, as shown in FIG. 8 (D), the k-space data $S1_{high}$ for generating the image corresponding to the parameter 1 can be extracted in a high frequency region where pieces of k-space data for generating the images corresponding to the parameters 2 and 3 are not acquired. Then, the k-space data S2 for generating the image corresponding to the parameter 2 can be acquired in the entire frequency region as shown in FIG. 8 (E) by composition of the extracted k-space data $S1_{high}$ for generating the image corresponding to the parameter 1 in the high frequency region and the k-space data $S2_{low}$ for generating the image corresponding to the parameter 2 in the low frequency region. Similarly, the k-space data S3 for generating the image corresponding to the parameter 3 can be acquired in the entire frequency region as shown in FIG. 8 (F) by composition of the extracted k-space data $S1_{high}$ for generating the image corresponding to the parameter 1 in the high frequency region and the k-space data $S3_{low}$ for generating the image corresponding to the parameter 3 in the low frequency region.

Note that, it is preferable that gains for acquiring the k-space data S1 for generating the image of the parameter 1, the k-space data $S2_{low}$ for generating the image of the parameter 2 and the k-space data $S3_{low}$ for generating the image of the parameter 3 are set to a common value from the viewpoint of a composition processing. When the k-space data $S2_{low}$ for generating the image of the parameter 2 is acquired so that the k-space data $S1_{high}$ for generating the image of the parameter 1 in the high frequency region overlaps with the k-space data $S2_{low}$ for generating the image of the parameter 2 in the low frequency region, in other words, when the k-space data $S2_{low}$ for generating the image of the parameter 2 is acquired so as to include a part of a region where the k-space data S1 for generating the image of the parameter 1 is used as a substitute, different species of parameter images can be generated without artificiality by a correction processing to reduce discontinuity among the pieces of k-space data to be combined with each other.

Although an example of a composition processing among pieces of k-space data is shown in FIG. 8, a composition processing among pieces of image data after an image reconstruction can be performed. The image reconstruction processing is performed in the image reconstruction unit 44.

Specifically, the image reconstruction unit 44 has a function for reconstructing image data, which is real space data, from k-space data by capturing the k-space data from the k-space database 42 and performing image reconstruction processing including FT (Fourier transformation) of the k-space data, and writing the generated image data to the image database 45. Therefore, the image database 45 stores respective pieces of image data, corresponding to mutually different parameters, reconstructed by the image reconstruction unit 44 and after-mentioned image data combined in the data composition unit 43.

The data composition unit 43 has the function to perform a composition processing among pieces of data for generating multiple different species of parameter images. In case of performing a composition processing among pieces of k-space data for generating multiple different species of parameter images, the data composition unit 43 is configured to read k-space data for generating a parameter image acquired for the entire frequency region and k-space data for generating another parameter image acquired for only a low frequency region from the k-space database 42, and to generate pieces of k-space data in the entire frequency region for generating all parameter images by a composition processing described above. The generated pieces of k-space data in the entire frequency region for generating the all parameter images are written into the k-space database 42.

Meanwhile, in case of performing a composition processing among pieces of image data corresponding to multiple different species of parameter images, the data composition unit 43 is configured to read pieces of image data respectively corresponding to the mutually different parameters from the image database 45, and generate multiple pieces of image data corresponding to the respective parameter values in the entire real space region by a composition processing of partial image data acquired for a part of real space region and image data, of a part to be combined with the partial image data, out of image data acquired for the entire real space region. The generated multiple pieces of image data corresponding to the respective parameter values in the entire real space region are written into the image database 45.

In addition, the data composition unit 43 has the function to perform a necessary correction processing of k-space data together with a composition processing among pieces of k-space data. For example, prior to a composition processing, a correction such as an amplitude (gain) correction, a phase correction and/or a sign inversion correction can be performed with respect to each of pieces of k-space data or image data corresponding to respective parameter values, namely, to be subjected to the composition processing. This can prevent data from deterioration such as ringing due to discontinuity in connection parts of the k-space data or the image data after composition processing. That is, a data continuity can be improved.

Note that, a composition processing may be performed among k-space data with performing a correction processing on image data. In this case, the data composition unit 43 is provided with the function to acquire pieces of k-space data for composition processing by performing IFT (inverse Fourier transformation) processing of pieces of image data after a correction processing.

An amplitude correction and a phase correction may be corrections for adjusting each amplitude and phase of pieces of k-space data or image data acquired for only a low frequency region to that of k-space data or image data having the maximum data volume acquired over the entire frequency region. The correction parameters such as gains for the amplitude correction and/or phase shift amounts for the phase correction can be calculated based on data in an overlapping part among pieces of data to be combined.

As shown in the formula (1) for example, a value derived by dividing an average value of absolute value data in an overlapping part $S_{1\_overlap}$ of the first k-space data $S_1$ acquired over the entire frequency region by an average value of absolute value data in an overlapping part $S_{N\_overlap}$ of the n-th (N=2, 3, 4, ..., Nmax) k-space data $S_N$ acquired for only a low frequency region can be set as a gain $G_N$ for an amplitude correction of the N-th k-space data $S_N$.

$$G_N = \text{ave}[\text{abs}(S_{1\_overlap})]/\text{ave}[\text{abs}(S_{N\_overlap})] \qquad (1)$$

Note that, in the formula (1), the abs(S) is a function that calculates an absolute value of a signal intensity S, and the ave(S) is a function that calculates an average value of signal intensity S. A gain for real space data can be determined based on an average value of absolute values in an overlapping part of image data in a similar way. Then, an amplitude correction can be performed by multiplying the determined gain by the data acquired for only the low frequency region targeted for composition. That is, an amplitude correction of data can be performed by considering a signal intensity ratio in an overlapping part among pieces of data to be synthesized as a gain.

Meanwhile, although a phase correction can be also performed on either k-space data or image data, it is easier to perform the phase correction on image data after the FT. In case of performing a phase correction on image data, phase shifts among pieces of image data can be successfully reduced by performing the phase correction on the nieces of image data after windowing in order to connect the pieces of image data smoothly in overlapping parts. In this case, a phase correction can be performed on partial image data obtained from k-space data acquired for only a low frequency region using reference image data obtained from a part in a low frequency region of k-space data acquired over the entire frequency region.

Specifically, as shown in the formula (2-1), image data $V_{1\_low}$ corresponding to a low frequency region is generated by multiplying the first k-space data $S_1$ acquired over the entire frequency region or a low frequency region part $S_{1\_low}$ of the first k-space data $S_1$ by a window function $W_{low}$ and FT. Similarly as shown in the formula (2-2), each image data $V_{N\_low}$ corresponding to a low frequency region is generated by multiplying a low frequency region part $S_{N\_low}$ of the N-th (N=2, 3, 4, ..., Nmax) k-space data $S_N$ acquired for only the low frequency region by the corresponding gain $G_N$ and the window function $W_{low}$ respectively and FT. Then, as for the N-th image data $V_{N\_low}$, a phase correction can be performed as shown in the formula (2-3) using a phase difference $\phi_1$ corresponding to a position difference between the image data $V_{1\_low}$ corresponding to the low frequency region of the first k-space data $S_1$ and each image data $V_{N\_low}$, after an amplitude correction, corresponding to the low frequency region of the N-th k-space data $S_N$. This can acquire the image data $V_{N\_low.cor}$ after an amplitude correction and a phase correction of the N-th k-space data $S_N$. That is, an amplitude difference and a phase difference among pieces of image data or k-space data to be combined can be eliminated.

$$V_{1\_low} = \text{FT}[W_{low} * S_{1\_low}] \qquad (2\text{-}1)$$

$$V_{N\_low} = \text{FT}[G_N * W_{low} * S_{N\_low}] \qquad (2\text{-}2)$$

$$V_{N\_low.cor} = V_{N\_low} * \exp(-j\phi 1) \qquad (2\text{-}3)$$

wherein N=2, 3, 4, ..., Nmax.

When tissue contrasts mutually become opposite among pieces of image data or k-space data to be combined as in the case where T1WI data and T2WI data are to be combined with each other, a sign inversion correction that inverts the sign of an arbitrary one of pieces of image data to be combined or an arbitrary one of pieces of k-space data to be combined is performed prior to a composition processing in the data composition unit 43.

A composition processing can be performed between pieces of k-space data or between pieces of image data as described above. In case of performing a composition between pieces of k-space data, a smooth composition can be performed by overlapping the pieces of k-space data to be combined with each other and multiplying the pieces of k-space data to be combined by the foregoing window function.

Figure 9:
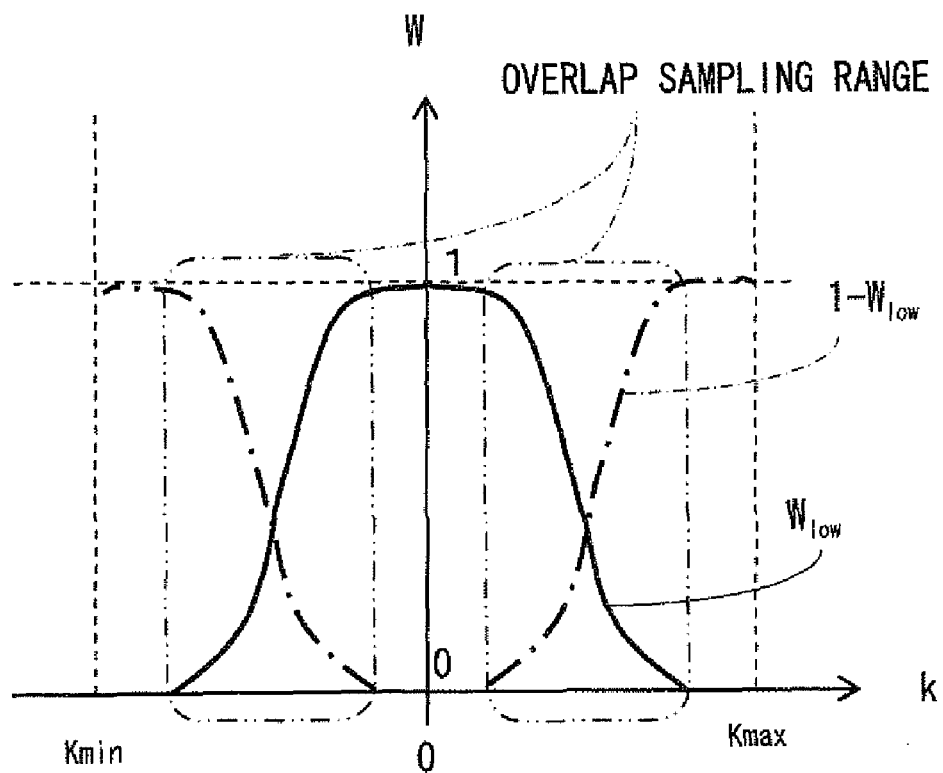
FIG. 9 is a graph showing an example of window function used for composition processing in the data composition unit shown in FIG. 7.

FIG. 9 is a graph showing an example of window function used for composition processing in the data composition unit 43 shown in FIG. 7.

In FIG. 9, the abscissa axis denotes an arbitrary axis direction k in k-space and the ordinate axis denotes weight W of the window function respectively. Kmin and Kmax in FIG. 9 indicate the minimum and the maximum of k-space data necessary for generating image data.

As shown in FIG. 9, a weighting function $W_{low}$ of which weight W in a part sampled with overlapping varies smoothly from 1 to 0 from a low frequency region toward a high frequency region is set as a window function applied in order to change the boundary part of the N-th k-space data $S_{N\_low}$ acquired for only a low frequency region smoothly. Meanwhile, a weighting function $1-W_{low}$ of which weight W in the part sampled with overlapping varies smoothly from 0 to 1 from the low frequency region toward the high frequency region is set as a window function in order to extract a part $S_{1\_high}$ in a high frequency region from the first k-space data $S_1$ acquired over the entire frequency region so that the boundary part becomes smooth.

In case of performing a composition processing among pieces of k-space data, k-space data $S_{N\_low.cor}$ after windowing, an amplitude correction and a phase correction can be acquired as shown in the formula (3) by performing IFT on the image data $V_{N\_low.cor}$, corresponding to the N-th low frequency region, subjected to windowing according to the weighting function $W_{low}$ shown in the formula (2-2) and after the phase correction, the FT and the amplitude correction shown in the formula (2-3). Then, as shown in the formula (3), k-space data $S_{N\_syn}$ over the entire frequency region after the composition processing can be acquired by adding the k-space data $S_{N\_low.cor}$ after correction in the low frequency region to the part $S_{1\_high}$ in the high frequency region extracted from the first k-space data $S_1$ by the windowing with the weighting function $1-W_{low}$.

$$S_{N\_syn} = (1-W_{low}) * S_1 + \text{IFT}[V_{N\_low.cor}] \quad (3)$$

The k-space data $S_{N\_syn}$, over the entire frequency region, synthesized as described above is written into the k-space database 42 and can be used for image reconstruction processing in the image reconstruction unit 44.

Meanwhile, in case of performing a composition processing among pieces of image data in the real space, image data $V_{1\_high}$ corresponding to the part $S_{1\_high}$ in the high frequency region is generated by extracting the part $S_{1\_high}$ in the high frequency region from the first k-space data $S_1$ by the windowing with the weighting function $1-W_{low}$ and performing the FT on the extracted the part $S_{1\_high}$ in the high frequency region as shown in the formula (4-1). Next, image data $V_{N\_syn}$, after composition processing, corresponding to the entire frequency region can be acquired by adding the image data $V_{1\_high}$ corresponding to the part $S_{1\_high}$ in the high frequency region to the n-th image data $V_{N\_low.cor}$, corresponding to the low frequency region, acquired by the formula (2-3). That is, each frequency component image data generated by the FT is added as complex data.

$$V_{1\_high} = \text{FT}[(1-W_{low}) * S_1] \quad (4\text{-}1)$$

$$V_{N\_syn} = V_{1\_high} + V_{N\_low.cor} \quad (4\text{-}2)$$

The image data $V_{N\_syn}$ over the entire frequency region synthesized as described above is written into the image database 45.

The image processing unit 46 has a function for generating pieces of two-dimensional image data for displaying by performing necessary image processing of the pieces of image data, corresponding to respective parameter values, after composition processing, read from the image database 45 and displaying the generated pieces of image data on the display unit 34.

When echo data is acquired by PI, unfolding processing of image data corresponding to each coil element 24c is necessary for generating unfolded image data. The unfolding processing is post-processing of PI performed based on conditions of PI. To that purpose, a function of performing unfolding processing is provided with the image processing unit 46. For unfolding processing, each sensitivity distribution of coil elements 24c is used.

The sensitivity distribution database 47 stores a sensitivity distribution of each coil element 24c necessary for an unfolding processing Then, the sensitivity distribution database 47 is configured to refer the stored sensitivity distribution data of each coil element 24c to the image processing unit 46.

(Operation and Action)

Then, the operation and action of the magnetic resonance imaging apparatus 20 will be described.

Figure 10:
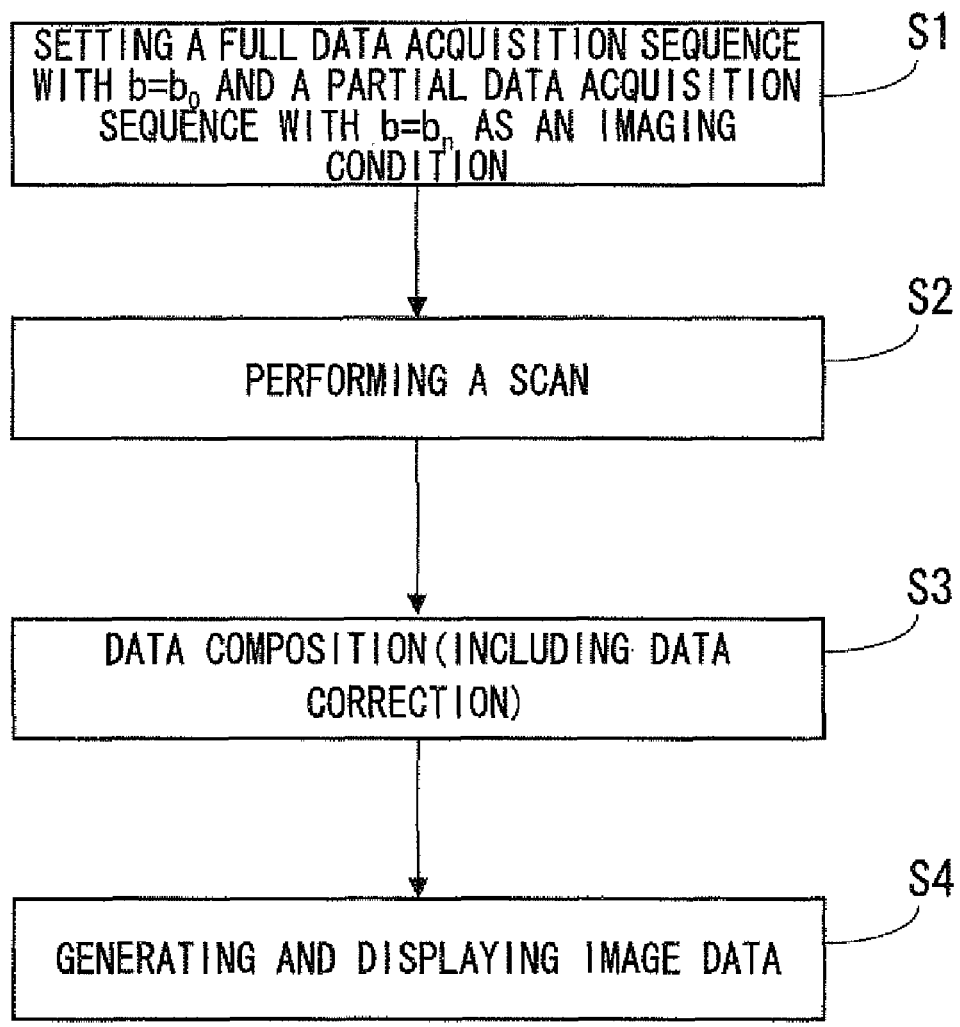
FIG. 10 is a flowchart showing a procedure of acquiring image data with setting the b-value, serving as an example of parameter value, to zero and a DWI with setting a b-value to non-zero from a same object by the magnetic resonance imaging apparatus shown in FIG. 3.

FIG. 10 is a flowchart showing a procedure of acquiring image data with setting the b-value, serving as an example of parameter value, to zero and a DWI with setting a b-value to non-zero from a same object P by the magnetic resonance imaging apparatus 20 shown in FIG. 3. The symbols each including S with a number in FIG. 10 indicate respective steps of the flowchart.

First in the step S1, a full data acquisition sequence for acquiring echo data in the entire frequency region without application of a MPG pulse, namely with setting $b=b_0 \square 0$, and a partial data acquisition sequence for acquiring echo data in only a low frequency region with setting a b-factor of a MPG pulse to $b_n > 0$ are set as imaging conditions respectively in the image condition setting unit 40. The application direction of the MPG pulse can be set to a single direction or the isotropic direction.

Figure 11:
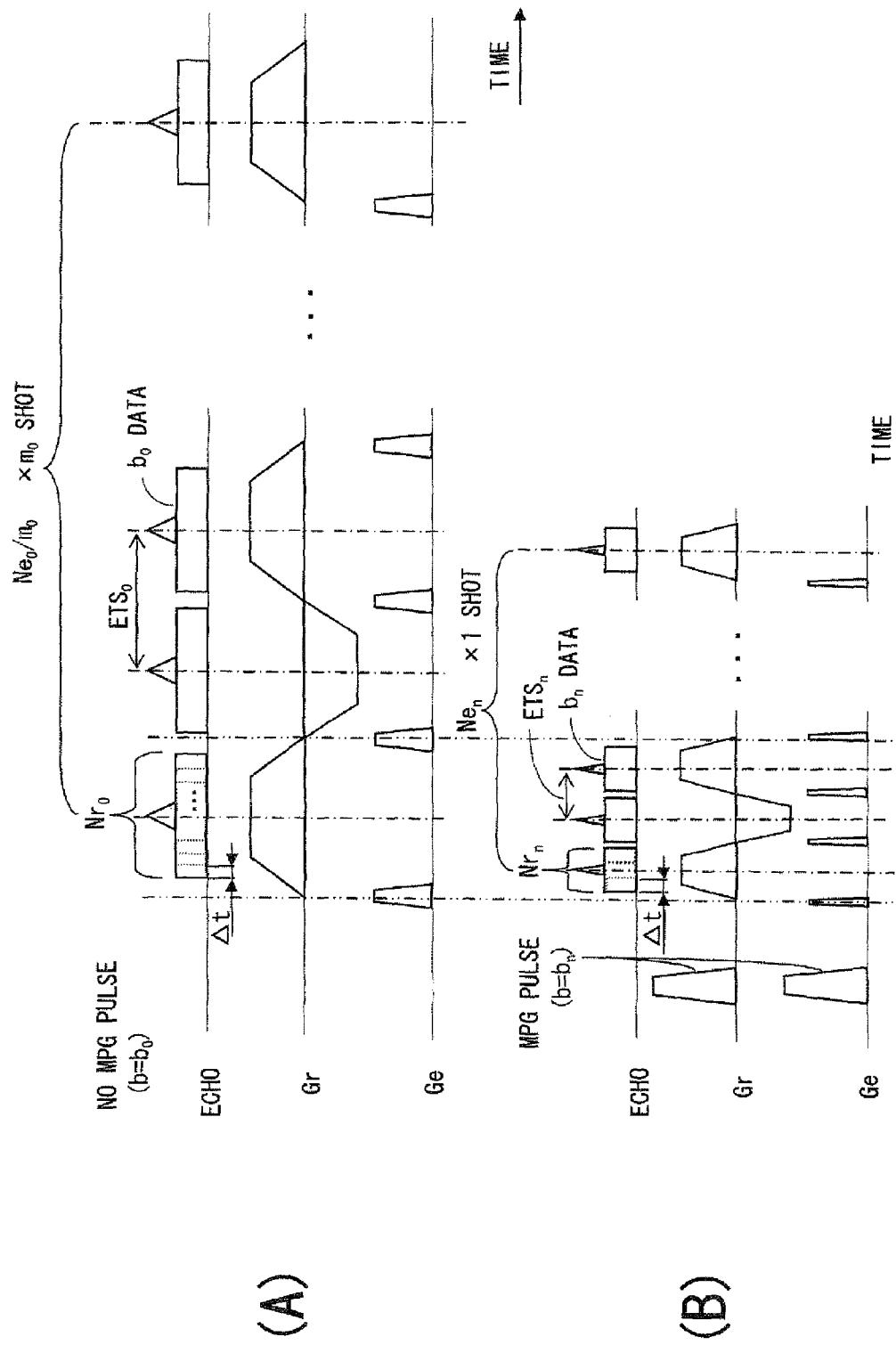
FIG. 11 is a chart showing an example of full data acquisition sequence for non-DWI and partial data acquisition sequence for DWI set in the imaging condition setting unit shown in FIG. 7.

FIG. 11 is a chart showing an example of full data acquisition sequence for non-DWI and partial data acquisition sequence for DWI set in the imaging condition setting unit 40 shown In FIG. 7.

In each of (A) and (B) of FIG. 11, ECHO, Gr and Ge denote echo data (magnetic resonance signals) to be acquired, gradient magnetic fields for readout and gradient magnetic fields for phase encode respectively.

A multi-shot EPI for acquiring data with m shots is generally under a data acquisition method for acquiring Ne/m echo signal trains per single RF excitation and arranging the echo signal trains in an encode direction in the k-space in the nested state, namely arranging the echo signal trains in an interleaved state at intervals of m like 1, m+1, 2m+1, . . . .

Specifically, as shown in FIG. 11 (A), an EPI sequence without application of a MPG pulse, namely with setting a b-factor to $b_0$ which can be regarded as zero, is set as a sequence to acquire a non-DWI for example. In the EPI sequence shown in FIG. 11 (A), a signal train consisting of echo signals of the sampling number $Nr_0$ is acquired $Ne_0/m_0$ times per single shot at a time interval $ETS_0$ with setting a sampling pitch for a single echo signal to a $\Delta t$. Therefore, the number of signal trains corresponding to the number $Ne_0$ of views is acquired in total by $m_0$ times multi-shot data acquisition. In the example shown in FIG. 11 (A), $m_0$=3. Consequently, k-space data ($b_0$ data) with setting b=$b_0$ can be acquired over the entire frequency region. Note that, use of PI is practical.

Meanwhile as shown in FIG. 11 (B), an EPI sequence with application of a MPG pulse with setting a b-factor to $b_n$ which is non-zero for example is set as a sequence for acquiring a DWI as the n-th image data. In the EPI sequence for the DWI shown in FIG. 11 (B), a single echo signal is acquired with a sampling pitch $\Delta t$, and a signal train consisting of echo signals of the sampling number $Nr_n$ is acquired $Ne_0/m_n$ times at a time interval $ETS_n$. In the example shown in FIG. 11 (B), $Ne_n$ echo signal trains are acquired at $m_n$=1, namely by single shot data acquisition. The use of the PI is also practical in case of acquiring $b_n$ data that is k-space data acquired with setting b=$b_n$.

Meanwhile, in the DWI, a single-shot data acquisition that acquires multiple pieces of echo data by a single excitation with a sequence such as an EPI sequence is mainly used. On the contrary, the echo train imaging for performing the multi-shot data acquisition that acquires multiple sets of echo data with multiple excitations and synthesizing the multiple sets of echo data in k-space is considered difficult to achieve in DWI since an artifact is generated due to a motion. Specifically, although navigation echo data for phase correction is acquired per shot and a phase correction is performed using the navigation echo data in case of performing the multi-shot data acquisition, a correction may not be performed with a satisfactory accuracy.

Accordingly, it is preferable that the sequence for the DWI is set as the EPI sequence for acquiring only $b_n$ data in a low frequency region that can be acquired by one shot as shown in FIG. 11 (B). This can suppress generation of an artifact by a motion. Thus, the $b_0$ data in the high frequency part acquired by the EPI sequence shown in FIG. 11 (A) can be used as data in the high frequency part to generate DWI data.

Therefore, it is preferable that the $b_0$ data in which an artifact due to a motion does not become problem is acquired by the multi-shot data acquisition with multiple excitations as shown in FIG. 11 (A) while the $b_n$ data is acquired by the single-shot data acquisition as shown in FIG. 11 (B) from the viewpoint of preventing generation of an artifact due to a motion. However, a phase shift between pieces of k-space data or a displacement between corresponding pieces of image data may be generated due to influence of a motion during acquisition of the $b_0$ data and the $b_n$ data at mutually different times t. To this matter, since k-space data at a center part of k-space is commonly used for generating each image data, a phase shift between pieces of k-space data or a displacement between corresponding pieces of image data due to a motion can be corrected by phase correction or position correction of the 2D or 3D k-space data or image data.

In addition, since the FOV in the readout direction is determined by the sampling pitch $\Delta t$, it is preferable that the sampling pitch $\Delta t$ is common between the EPI sequence for $b_0$ data acquisition and the EPI sequence for $b_n$ data acquisition. However, the sampling pitch $\Delta t$ in the readout direction is sufficiently small compared to an ETS corresponding to the sampling pitch in the encoding direction. Therefore, even if the sampling pitch $\Delta t$ differs a little between the EPI sequence for the $b_0$ data and the EPI sequence for the $b_n$ data, the difference does not influence distortion in the readout direction so much and does not become a big problem.

Note that, data for generating T2WI data may be acquired using an FSE sequence as $b_0$ data in the entire frequency region. In case of acquiring $b_0$ data by an FSE sequence, a distortion correction or a contrast correction of $b_n$ data in a low frequency region acquired by an EPI sequence becomes necessary. In case of acquiring both $b_0$ data and $b_n$ data by FSE sequences, data acquisition conditions of the $b_0$ data and the $b_n$ data increase flexibility since there is no restriction caused by distortion of image data.

On the contrary, in case of acquiring both $b_0$ data and $b_n$ data by EPI sequences as shown in FIG. 11, setting imaging conditions including an $ETS_0$, an $ETS_n$, the numbers of views $Ne_0$ and $Ne_n$ which are the numbers of lines in encode directions, the sampling numbers $Nr_0$ and $Nr_n$ in readout directions and a speed scale rate of PI according to certain conditions described hereinbelow can make distortions in pieces of image data acquired from the $b_0$ data and the $b_n$ data respectively be mutually equivalent. In addition, a basic contrast due to each factor other than diffusion effect also becomes equivalent between pieces of image data acquired from the $b_0$ data and the $b_n$ data respectively. Therefore, in case of acquiring both $b_0$ data and $b_n$ data by EPI sequences, a distortion correction and a contrast correction of $b_n$ data become unnecessary.

A distortion of image data acquired by an EPI sequence is large in a phase encode direction, and determined by an effective ETS ($ETS_{effective}$). Specifically, a distortion of image data decreases in a smaller $ETS_{effective}$. An $ETS_{effective}$ becomes equal to 1/m times an ETS for one shot when the number of shots is represented by m. When a speed scale rate R of PI is multiplied by "a" to be a-times, an $ETS_{effective}$ becomes equal to 1/a times an ETS for a speed-scale-rate-of-PI R=1. Therefore, if imaging conditions for $b_0$ data and $b_n$ data acquisitions are set so that the formula (5) can be established, the ETSes can become mutually equal effectively.

$$ETS_{effective}=ETS_n/R_n=ETS_0/(m_0*R_0) \quad (5)$$

Note that, in the formula (5), $R_n$ represents a speed scale rate of PI for $b_n$ data acquisition, $R_0$ represents a speed scale rate of PI for $b_0$ data acquisition, and $m_0$ which is a natural number represents the number of shots for $b_0$ data acquisition.

Specifically, setting imaging conditions for $b_0$ data and $b_n$ data acquisitions as shown in the formula (5) so that the ratio ($ETS_n/R_n$) of the $ETS_n$ for the $b_n$ data acquisition to the speed scale rate $R_n$ of PI becomes $1/m_0$ of the ratio ($ETS_0/R_0$) of the $ETS_0$ for the $b_0$ data acquisition to the speed scale rate $R_0$ of PI can make distortions of pieces of image data respectively acquired from the $b_n$ data and the $b_0$ data mutually equal. Consequently, distortion corrections of the $b_n$ data and/or the $b_0$ data become unnecessary.

Moreover, if sampling pitches $\Delta t$ of the $b_n$ data and the $b_0$ data are the same and there is no overlapping part in pieces of data to be synthesized, a ratio of the number of views $Ne_0$ of the $b_0$ data to the number of views $Ne_n$ of the $b_n$ data becomes $m_0$ as shown in the formula (6-1). Meanwhile, when there is an overlapping part in pieces of data to be synthesized, the formula (6-2) is formed.

$$Ne_0/Ne_n=m_0 \quad (6-1)$$

$$Ne_0/Ne_n<m_0 \quad (6-2)$$

Therefore, if $R_0=m_0*R_n$ is formed between the speed scale rate $R_0$ of PI for the $b_0$ data acquisition and the speed scale rate $R_n$ of PI for the $b_n$ data acquisition, the ETS for the $b_n$ data acquisition and the ETS for the $b_0$ data acquisition can be set to a same value, namely $ETS_n=ETS_0$, according to the formula (5). Further, from the formula (6), It is necessary to set imaging conditions so that the formula (7) can be formed in order to set a SNR (signal to noise ratio) of the $b_n$ data to more than or equivalent to that of the $b_0$ data.

$$NAQ_0 \geq m_0 * NAQ_n \tag{7}$$

Note that, $NAQ_0$ represents the number of pieces of data that is subject to an averaging processing in case of generating image data by performing the averaging processing of multiple pieces of $b_0$ data and $NAQ_n$ represents the number of pieces of data that is subject to averaging processing in case of generating DWI data by performing averaging processing of multiple pieces of $b_n$ data.

According to the formula (5), even if the speed scale rate $R_0$ of PI for the $b_0$ data acquisition and the speed scale rate $R_n$ of PI for the $b_n$ data acquisition are set to mutually equal, namely $R_n=R_0$, setting the numbers of views $Ne_0$ and $Ne_n$ so that a ratio of the number of views of the $b_0$ data to that of the $b_n$ data becomes $m_0$ as shown in the formula (6), namely $Ne_0/Ne_n=m_0$ can make $ETS_0=m_0*ETS_n$ and the formula (5) formed.

Therefore, if the sampling pitches $\Delta t$ for the $b_0$ and $b_n$ data acquisitions are the same and a waveform of each readout gradient magnetic field Gr is rectangle, imaging conditions can be set so that the formula (5) can be formed. Even if the waveform of each readout gradient magnetic field Gr is trapezoid, imaging conditions can be set so that $ETS_0 \square m_0*ETS_n$ is formed by performing the ramp sampling that performs sampling in inclined parts including a rise and a decay. Moreover, if it is difficult to form the condition shown in the formula (5) by adjusting only the numbers of views $Ne_0$ and $Ne_n$, the condition shown in the formula (5) can be formed by adjusting the speed scale rates $R_0$ and $R_n$ of PI, the sampling pitch $\Delta t$ in a readout direction and/or the sampling numbers $Nr_0$ and $Nr_n$ in a readout direction.

Note that, in the example shown in FIG. 11, the speed scale rates $R_n$ and $R_0$ of PI are the same, namely $R_n=R_0$ and $Ne_0/Ne_n=Nr_0/Ne_n=ETS_0/ETS_n=m_0=3$ with mutually different numbers of shots. The ratio ($Ne_0/Ne_n$) of the number of views $Ne_0$ corresponding to the sampling number in a phase encode direction to the number of views $Ne_n$ and the ratio ($Nr_0/Nr_n$) of the sampling number $Nr_0$ to the sampling number $Nr_n$ in a readout direction can be set independently.

As shown in FIG. 11, when $Ne_0/Ne_n=Nr_0/Nr_n=ETS_0/ETS_n=m_0$ is formed, setting the speed scale rates $R_n$ and $R_0$ of PI so that $R_n=m_0R_0$ can be formed with the same number of shots for the $b_0$ data and the $b_n$ data, the effect similar to the case shown in FIG. 11 can be achieved since a difference $m_0=Ne_0/Ne_n$ in the speed scale rate of PI can be regarded as equivalent to sampling by a difference, corresponding to the difference between the speed scale rates, in the numbers of pieces of data. Moreover, when $Ne_0/Ne_n=Nr_0/Nr_n=ETS_0/ETS_n=m_0$ is formed, the effect similar to the case shown in FIG. 11 can be achieved as long as the formula (5) is formed even if both the numbers of shots and the speed scale rates of PI are different between the $b_0$ data and the $b_n$ data.

Figure 12:
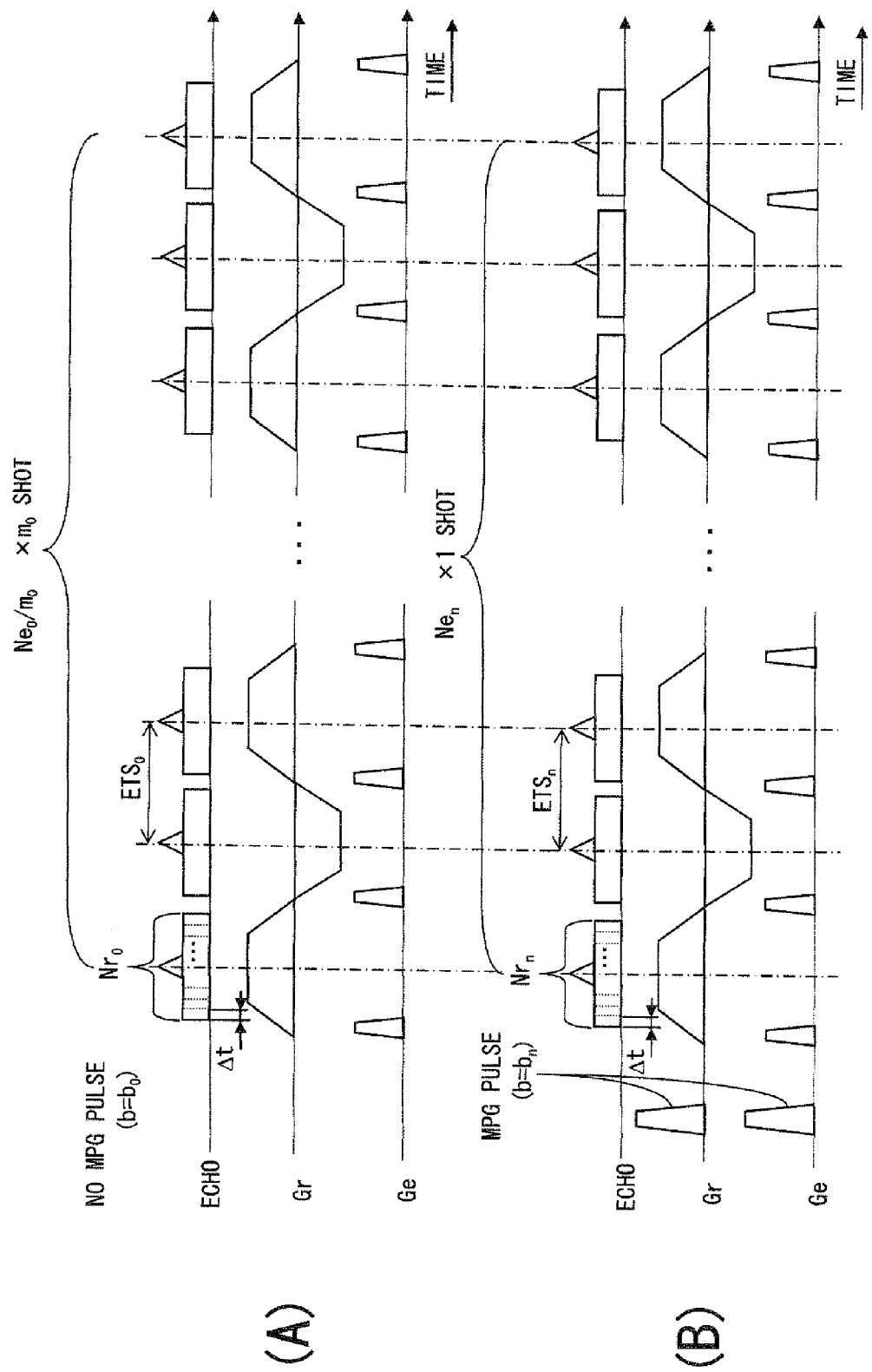
FIG. 12 is a chart showing another example of full data acquisition sequence for non-DWI and partial data acquisition sequence for DWI set in the imaging condition setting unit shown in FIG. 7.

FIG. 12 is a chart showing another example of full data acquisition sequence for non-DWI and partial data acquisition sequence for DWI set in the imaging condition setting unit 40 shown in FIG. 7.

In each of (A) and (B) of FIG. 12, ECHO, Gr and Ge denote echo data (magnetic resonance signals) to be acquired, gradient magnetic fields for readout and gradient magnetic fields for phase encode.

As shown in FIG. 12 (A), a multi shot EPI sequence that acquires a signal train consisting of a sampling number $Nr_0$ of echo signals $Ne_0/m_0$ times per single shot at a time interval $ETS_0$ with a sampling pitch $\Delta t$ can be set as a sequence for $b_0$ data acquisition, Therefore, the number of signal trains corresponding to the number of views $Ne_0$ in total is acquired by multi shot data acquisitions over $m_0$ times. FIG. 12 (A) shows an example of $m_0=3$.

Meanwhile, as shown in FIG. 12 (B), a single shot EPI sequence that acquires a signal train consisting of the sampling number $Nr_n$ of echo signals $Ne_n$ times at a time interval $ETS_n$ with a sampling pitch $\Delta t$ can be set as a sequence for $b_n$ data acquisition.

Note that, the sampling number $Nr_0$ of the $b_0$ data and the sampling number $Nr_n$ of the $b_n$ data, the $ETS_0$ of the $b_0$ data and the $ETS_n$ of the $b_n$ data, the number of signal trains $Ne_0/m_0$ of the $b_0$ data per shot and the number of signal trains $Ne_n$ of the $b_n$ data are set to the same values, respectively. Though imaging conditions are set so as to form $Nr_0/Nr_n=1$, $Ne_0/Ne_n=m_0$ and $ETS_0/ETS_n=1$ as described above, the $ETS_{effective}$ can become equal as shown in the formula (8) by setting the speed scale rates $R_n$ and $R_0$ of PI so that $R_0=R_n/m_0$.

$$ETS_{effective}=ETS_0/m_0=ETS_n/m_0 \tag{8}$$

When imaging conditions are set as described above, scans are performed according to the set imaging conditions in the step S2 subsequently.

That is, the object P is set to the bed 37, and a static magnetic field is generated at an imaging area of the magnet 21 (a superconducting magnet) for static magnetic field excited by the static-magnetic-field power supply 26. Further, the shim-coil power supply 28 supplies current to the shim coil 22, thereby uniformizing the static magnetic field generated at the imaging area.

Then, the input device 33 sends instruction of starting a scan to the sequence controller control unit 41. The sequence controller control unit 41 supplies the sequence for acquiring $b_0$ data in the whole frequency region and the sequence for acquiring $b_n$ data only in the low frequency region subsequently received from the imaging condition setting unit 40 to the sequence controller 31. Therefore, the sequence controller 31 drives the gradient power supply 27, the transmitter 29, and the receiver 30 in accordance with the pulse sequences received from the sequence controller control unit 41, thereby generating a gradient magnetic field at the imaging area having the set object P, and further generating RF signals from the RF coil 24.

Consequently, the RF coil 24 receives NMR signals generated due to nuclear magnetic resonance in the object P. Then, the receiver 30 receives the NMR signals from the RF coil 24 and generates raw data which is digital data of NMR signals by A/D conversion subsequently to necessary signal processing. The receiver 30 supplies the generated raw data to the sequence controller 31. The sequence controller 31 supplies the raw data to the sequence controller control unit 41. The sequence controller control unit 41 arranges the raw data as k-space data to the k space formed in the k-space database 42.

Consequently, $b_0$ data in the entire frequency region is arranged in the first k-space of the k-space database 42, and $b_n$ data in only the low frequency region is arranged in the second k-space of the k-space database 42.

Next, in the step S3, data composition processing is performed in the data composition unit 43. In addition, processing such as windowing, a phase correction and an amplitude correction as described above is performed on the $b_0$ data, the $b_n$ data, real space data acquired from the $b_0$ data, and/or real space data acquired from the $b_n$ data prior to composition processing as needed. Hereinafter a case of composition processing between pieces of k-space data after necessary preprocessing will be described.

Figure 13:
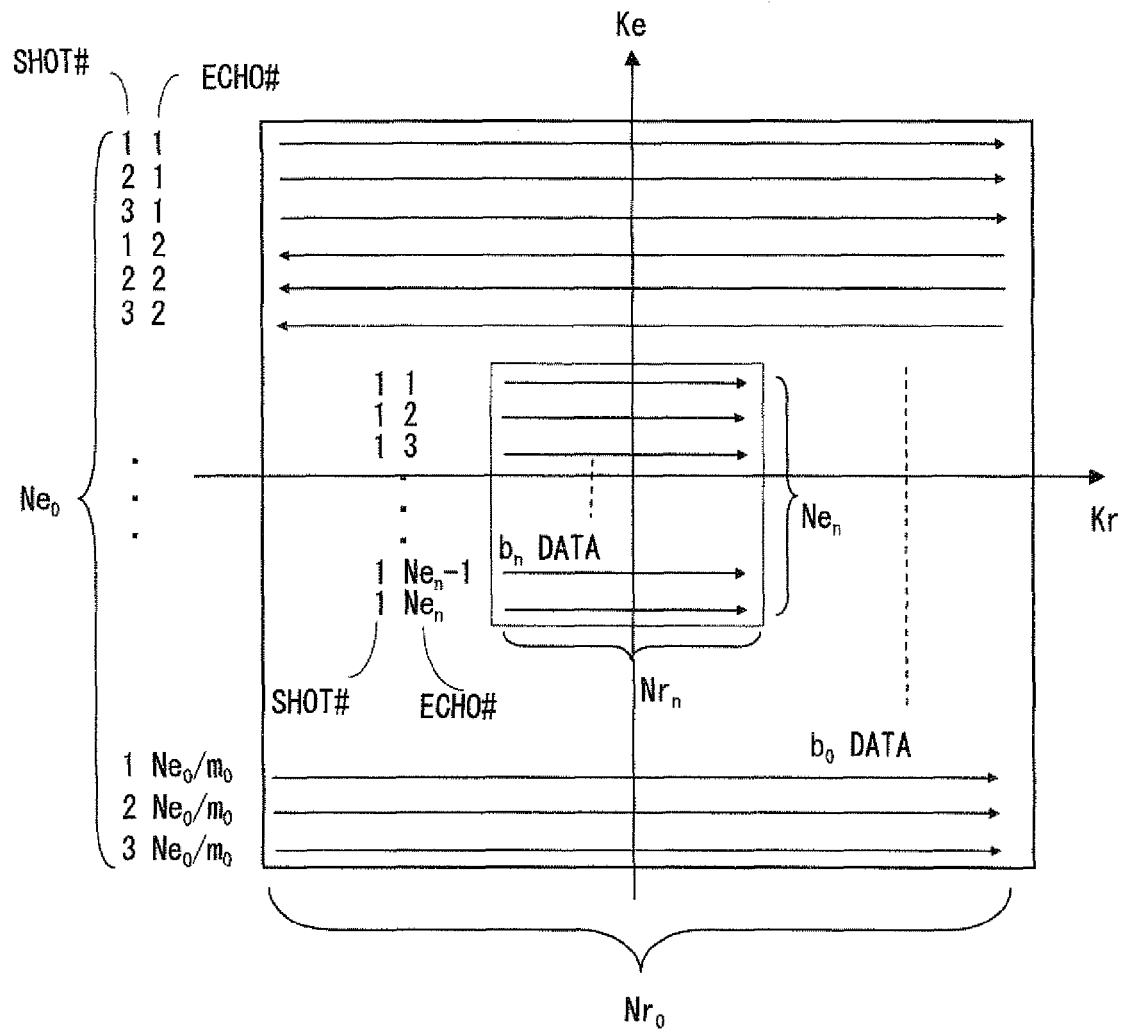
FIG. 13 is a graph showing an example of composition of the k-space data acquired by the two types of the EPI sequence shown in FIG. 11.

FIG. 13 is a graph showing an example of composition of the k-space data acquired by the two types of the EPI sequence shown in FIG. 11.

In FIG. 13, the abscissa axis denotes the readout direction Kr in k-space and the ordinate axis denotes the phase encode direction Ke in k-space. As shown in FIG. 13, the $b_n$ data is arranged in a low frequency region. Specifically, k-space data of the number equivalent to the number of views $Ne_n$ and the sampling number $Nr_n$ with one shot is arranged as the $b_n$ data. Meanwhile, $b_0$ data in a high frequency region having no $b_n$ data is extracted out of the $b_0$ data in the entire frequency region and arranged around the $b_n$ data. In the example shown in FIG. 13, since the $b_0$ data is acquired with three shots, the $b_0$ data consists of k-space data of the number equivalent to the number of views $Ne_0$ and the sampling number $Nr_0$ corresponding to each shot.

Figure 14:
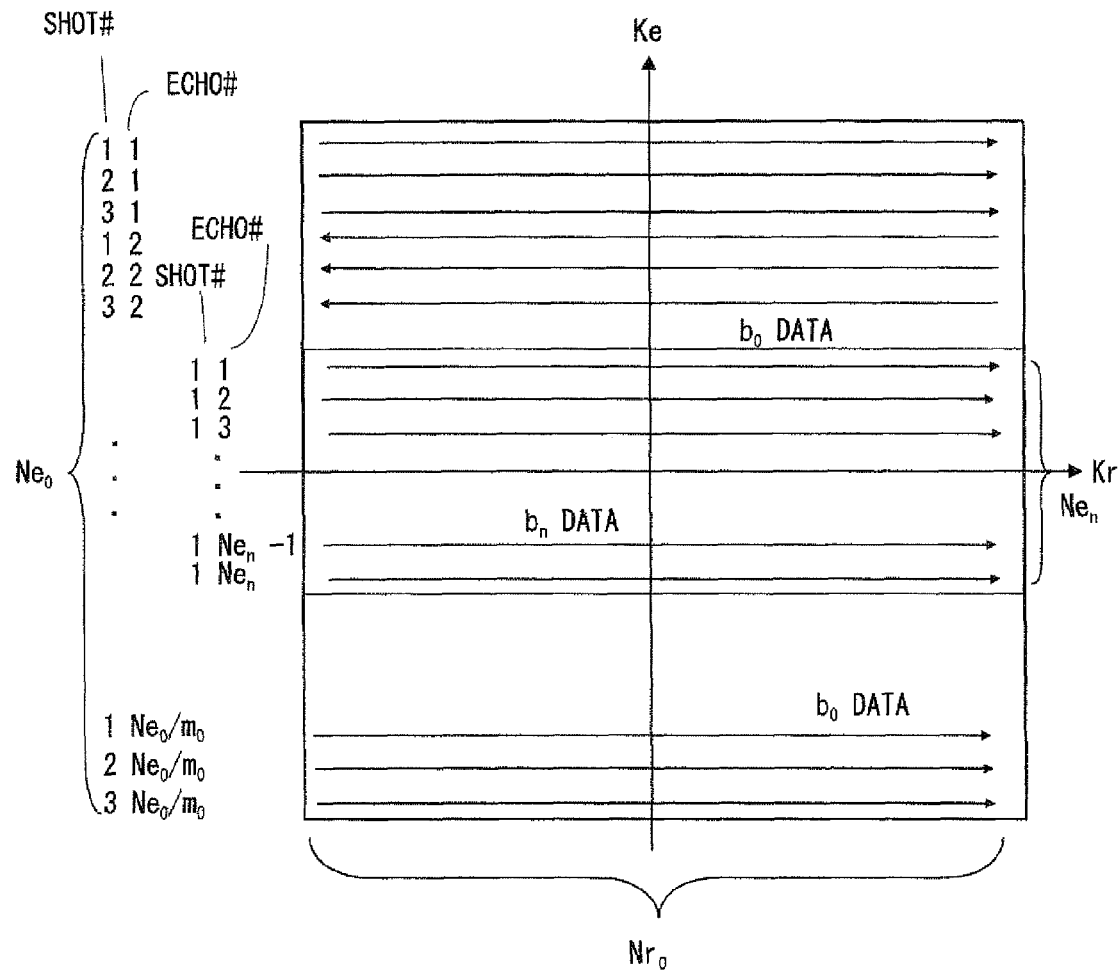
FIG. 14 is a graph showing an example of composition of the k-space data acquired by the two types of the EPS sequence shown in FIG. 12.

FIG. 14 is a graph showing an example of composition of the k-space data acquired by the two types of the EPI sequence shown in FIG. 12

In FIG. 14, the abscissa axis denotes the readout direction Kr in k-space and the ordinate axis denotes the phase encode direction Ke in k-space. The $b_n$ data is arranged as shown in FIG. 14. Specifically, k-space data of the number equivalent to the number of views $Ne_n$ and the sampling number $Nr_n$ with one shot is arranged as the $b_n$ data. Since the sampling number $Nr_n$ of the $b_n$ data in the readout direction is equal to the sampling number $Nr_0$ of the $b_0$ data in the readout direction in the entire frequency region, the $b_n$ data is arranged over the entire frequency region in the readout direction. On the other hand, the $b_n$ data is arranged in a low frequency region in the phase encode direction.

Meanwhile, $b_0$ data in a high frequency region having no $b_n$ data in the phase encode direction is extracted out of the $b_0$ data in the entire frequency region and arranged on both sides of the $b_n$ data. In the example shown in FIG. 13, since the $b_0$ data is acquired with three shots, the $b_0$ data consists of k-space data of the number equivalent to the number of views $Ne_0$ and the sampling number $Nr_0$ corresponding to each shot.

When two types of EPI sequence are set shown in FIG. 12, $b_0$ data in the entire frequency region in the readout direction can be acquired as shown in FIG. 14.

In the step S4, plural pieces of image data with different contrasts are generated. Specifically, when data after composition processing is k-space data, image reconstruction processing is performed on the k-space data after composition processing and the k-space data acquired in the entire frequency region in the image reconstruction unit 44. Two types of image data acquired by the image reconstruction processing are stored in the image database 45. Meanwhile, when data after composition processing is image data, the image data after composition processing is stored in the image database 45 together with image data obtained by image reconstruction processing of the k-space data acquired in the entire frequency region by the image reconstruction unit 44.

Then, the image processing unit 46 reads the image data after composition processing and the image data obtained by image reconstruction processing of the k-space data acquired in the entire frequency region from the image database 45, performs necessary image processing and displays the image data simultaneously or sequentially on the display unit 34. For example, when echo data is acquired by PI, unfolding processing is performed on plural pieces of image data corresponding to respective coil elements 24c in the image processing unit 46 based on sensitivity distribution data of each coil element 24c stored in the sensitivity distribution database 47.

Since the multiple pieces of image data displayed as described above have common k-space data in the low frequency region, the pieces of image data can be acquired in a shorter imaging time.

Consequently, a user can acquire multiple pieces of image data of a same object P with mutually different contrasts in a shorter time.

That is, the foregoing magnetic resonance imaging apparatus 20 is an apparatus which shares a part of k-space data in case of imaging different species of parameter images such as a T1WI, a T2WI, a PDWI, a FLAIR image, a DWI and a PWI for a same object P, and performs data composition processing to shorten an imaging time without reduction of an amount of information. For example, data of in a high frequency region of k-space is shared among different species of parameter images, and only data in a low frequency region of k-space is acquired for respective different species of parameter images. Then, parameter image data with maintaining a data quality can be generated by combining the data acquired in only the low frequency region after amplitude correction and/or phase correction with the data in the high frequency region. Moreover, in case of performing an imaging of DWIs with different b-factors by EPI sequences, imaging conditions including the ETS, the number of shots and the speed scale rate of PI are set to predetermined conditions so that distortions of the respective pieces of image data becomes mutually equivalent.

(Effect)

According to the magnetic resonance imaging apparatus 20, a total imaging time can be shortened with maintaining an image quality and an amount of information in case of imaging multiple different species of parameter images of a same object P.

In addition, 3D-DWI data that is difficult to be acquired now or in the future by a single shot data acquisition with a sequence such as an EPI sequence having restriction in a FOV, a time resolution and a time resolution because of various restrictions including restriction of a hardware such as a gradient magnetic field generating system and restriction of the slew rate derived from nerve stimulation can become only data that can be acquired with one shot by utilizing other parameter image data effectively. Consequently, a DWI with suppressed artifact by a motion can be acquired. Note that, the slew rate is a value derived by dividing an intensity of gradient magnetic field by a necessary rising time for acquiring the intensity of the gradient magnetic field. As the slew rate increases, the variation dB/dt of magnetic field per unit time becomes large and the peripheral nerve stimulation might be destructive to the security of a patient.

(Modification)

1. First Modification

Although composition processing of two pieces of data was described in the example described above, composition processing of more than two pieces of data can be also performed.

Figure 15:
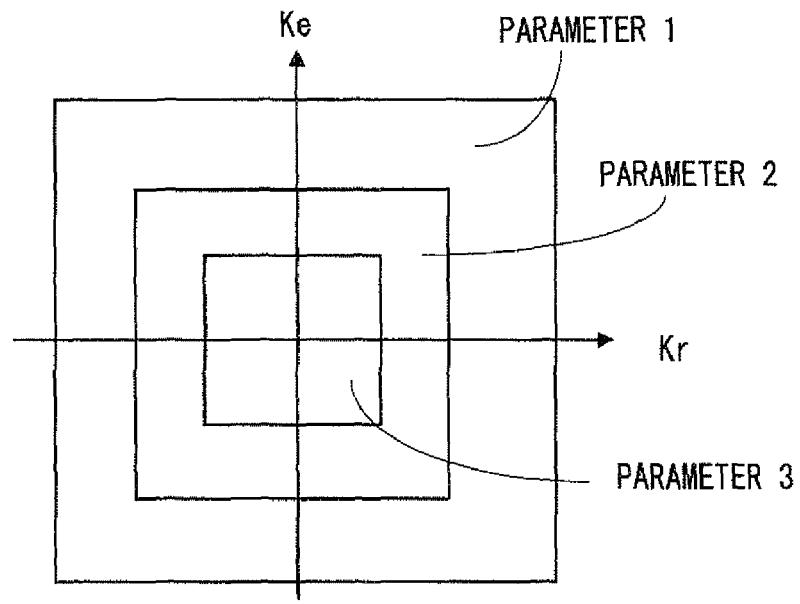
FIG. 15 is a graph showing a case of performing composition processing of three pieces of k-space data in the data composition unit shown in FIG. 7.

FIG. 15 is a graph showing a case of performing composition processing of three pieces of k-space data in the data composition unit 43 shown in FIG. 7.

In FIG. 15, the abscissa axis denotes the readout direction Kr in k-space and the ordinate axis denotes the phase encode direction Ke in k-space. As shown in FIG. 15, it is possible to set more than two parameter sets each consisting of plural parameters so that at least one value of a parameter set becomes different from that of another parameter set to acquire pieces of k-space data corresponding to the respective parameter sets and perform composition processing of the acquired pieces of k-space data. In the example shown in FIG. 15, pieces of k-space data (PARAMETER 1, PARAMETER 2, PARAMETER 3), in a high frequency region, a middle frequency region and a low frequency region, corresponding to three types of parameter sets of which a value of at least one parameter is different from each other is combined for single image data.

As a method for arranging multiple pieces of k-space data in k-spacer it is preferable to arrange a piece of k-space data corresponding to a pieces of image data with a contrast similar to a desired contrast out of multiple pieces of image data obtained from the respective pieces of k-space data in the center of k-space from the viewpoint of acquiring the desired contrast. In addition, it is preferable to arrange the other pieces of k-space data from a piece of k-space data corresponding to a piece of image data with a contrast more similar to the desired contrast sequentially from a low frequency region side toward the high frequency region. Therefore, it is preferable to acquire a piece of k-space data corresponding to each parameter set in the low frequency region. Note that, an imaging time is approximately proportional to a data amount equivalent to an area of k-space.

Figure 16:
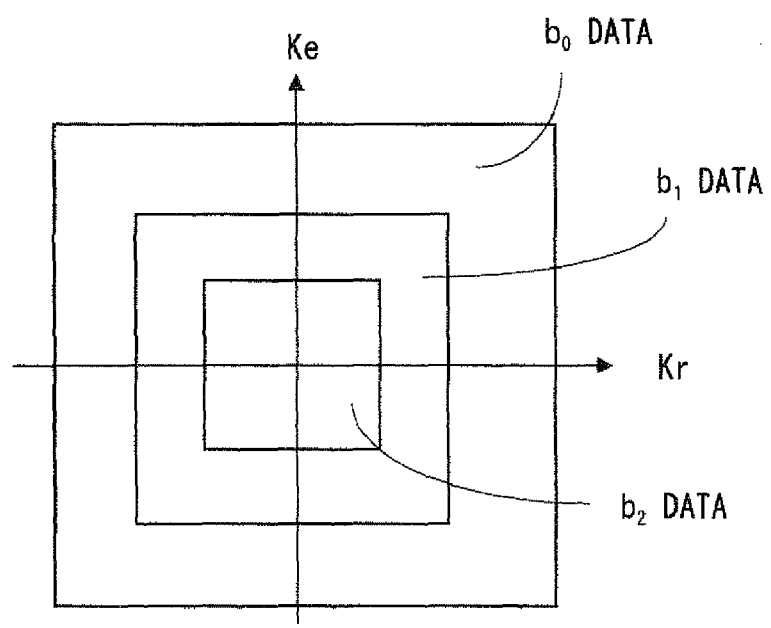
FIG. 16 is a graph showing a case of performing composition processing of three pieces of k-space data corresponding to mutually different b values in the data composition unit shown in FIG. 7.

FIG. 16 is a graph showing a case of performing composition processing of three pieces of k-space data corresponding to mutually different b values in the data composition unit 43 shown in FIG. 7.

In FIG. 16, the abscissa axis denotes the readout direction Kr in k-space and the ordinate axis denotes the phase encode direction Ke in k-space. As shown in FIG. 15, it is possible to pieces of k-space data ($b_0$ DATA, $b_1$ DATA and $b_2$ DATA) by setting the b-factor to not only two steps of b=$b_0$ and b=$b_n$, but three steps of b=$b_0$, b=$b_1$ and b=$b_2$ (0≦$b_0$<$b_1$<$b_2$), and perform composition processing of the acquired pieces of k-space data.

In this case, for generating DWI data with a contrast corresponding to the $b_2$ DATA, data may be arranged in the order of the $b_2$ DATA, the $b_1$ DATA and the $b_0$ DATA outward from the center side of k-space. Specifically, since the center part of k-space is the $b_2$ DATA, DWI data with the contrast corresponding to the $b_2$ DATA can be generated. In case of generating DWI data with a contrast corresponding to the $b_1$ DATA, data may be arranged in the order of the $b_1$ DATA and the $b_0$ DATA outward from the center part of k-space without using the $b_2$ DATA.

In other words, in case of acquiring k-space data by setting the b-factor to more than mutually different two values, it is preferable to arrange k-space data so that the b-factor corresponding to k-space data after composition processing varies smoothly from the viewpoint of keeping contrast continuity. Specifically, it is preferable to arrange multiple pieces of k-space data from the center part of k-space toward a high frequency side in the descending order of amplitude of the b-factor.

Note that, pieces of k-space data can be acquired by changing the foregoing m value in phase like m=5, m=3 and m=1 with setting the b-factor and an application direction of a MPG pulse to the same. On the contrary, by setting not only the b-factor but an application direction of a MPG pulse to mutually different directions, corresponding pieces of k-space data can be acquired. In this case, setting the isotropic direction as one of application directions of a MPG pulse and arranging a piece of k-space data acquired by applying the MPG pulse in the isotropic direction in the center part of k-space can improve continuity of generated image data.

Figure 17:
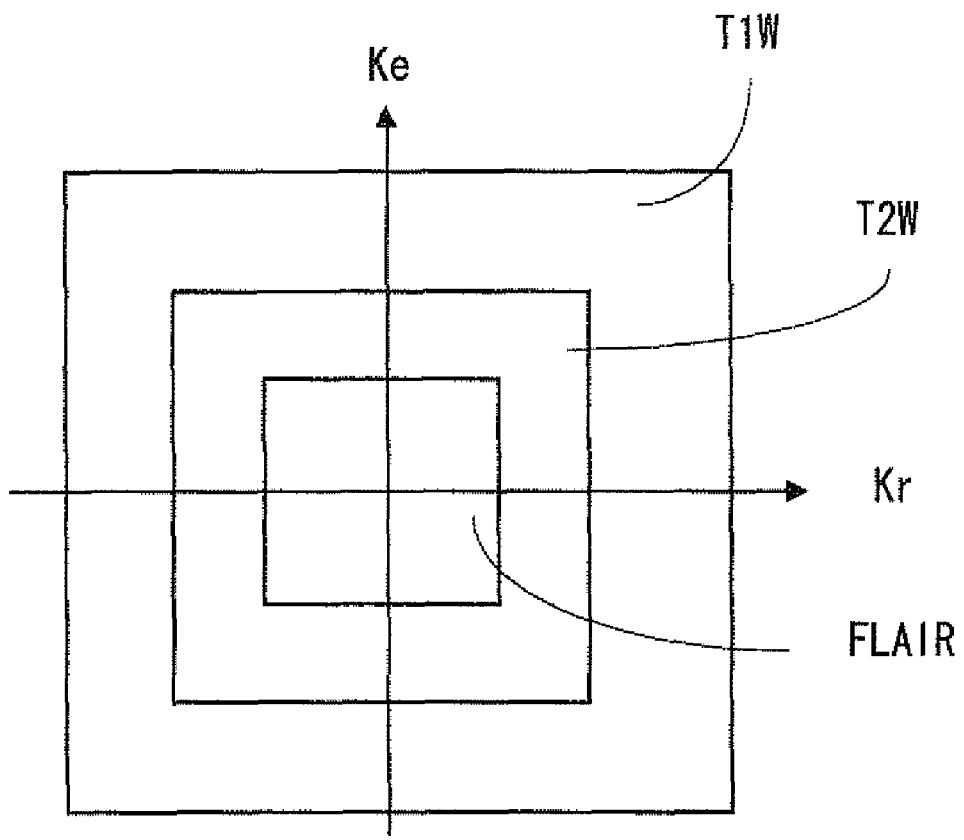
FIG. 17 is a graph showing a case of performing composition processing of three pieces of k-space data for a FLAIR image, a T1WI and a T2WI in the data composition unit shown in FIG. 7.

FIG. 17 is a graph showing a case of performing composition processing of three pieces of k-space data for a FLAIR image, a T1WI and a T2WI in the data composition unit 43 shown in FIG. 7.

In FIG. 17, the abscissa axis denotes the readout direction Kr in k-space and the ordinate axis denotes the phase encode direction Ke in k-space. As shown in FIG. 17, three pieces of k-space data for a FLAIR image, a T1WI and a T2WI can be acquired and composition processing can be performed on the acquired pieces of k-space data. FIG. 17 shows k-space data for generating the FLAIR image, and therefore, a piece of k-space data in the center part of k-space is k-space data for the FLAIR image. Further, from the viewpoint of improving contrast continuity, the k-space data for the T2WI is arranged in a middle frequency region in k-space and the k-space data for the T1WI is arranged in a high frequency region in k-space respectively.

Moreover, composition processing can also be performed on multiple pieces of k-space data in N regions determined regardless of a low frequency region or a high frequency region.

2. Second Modification

Although acquiring k-space data in a Cartesian state was described in the foregoing example, k-space data can be acquired in a Non Cartesian state. In addition to radial acquisition, the PROPELLER (periodically rotated overlapping parallel lines with enhanced reconstruction) method (also called the BLADE method) that rotates a band region called a blade formed by multiple parallel data acquisition loci per a repetition time is known as a technique to acquire k-space data in a Non Cartesian state.

Figure 18:
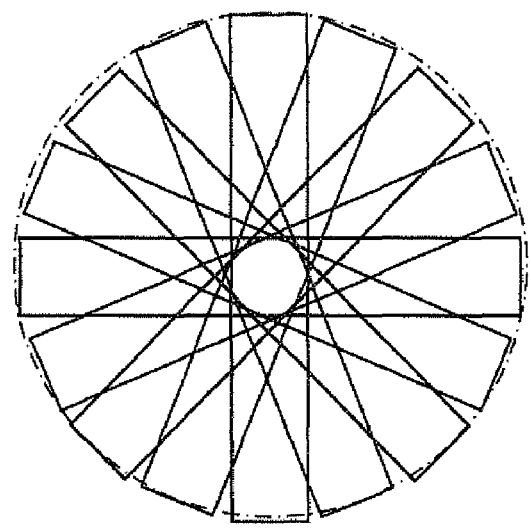
FIG. 18 is a diagram showing an example of data acquisition by a PROPELLER method.
Figure 18:
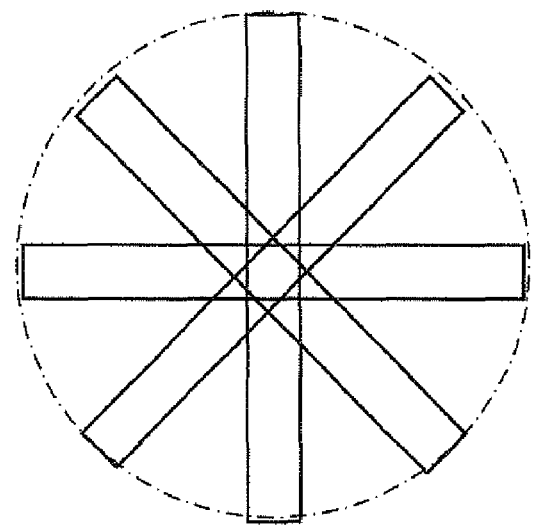

FIG. 18 is a diagram showing an example of data acquisition by a PROPELLER method.

FIG. 18 (A) shows an arrangement of k-space data ($b_0$ data) acquired with setting b=$b_0$ on k-space. FIG. 18 (B) shows an arrangement of k-space data ($b_n$ data) acquired with setting b=$b_n$>0 on k-space.

As shown in (A) and (B) of FIG. 18, in case of acquiring data by a PROPELLER method, the data becomes denser and is acquired with overlaps at nearer the center of k-space. For example, in case of acquiring DWI data, the DWI data can be acquired by the composition of the $b_0$ data and the $b_n$ data in the data composition unit 43 as described above.

At this time, as shown in FIGS. 18 (A) and (B), setting imaging conditions so that each step angle of blade to acquire the $b_n$ data is larger than that to acquire the $b_0$ data can reduce a data amount of the $b_n$ data. Moreover, the data amount of the $b_n$ data can be reduced by setting the imaging conditions so that each blade width to acquire the $b_n$ data is narrower than that to acquire the $b_0$ data as well. In other words, a data amount to be acquired can be reduced by acquiring the $b_n$ data coarsely with acquiring the $b_0$ data densely.

Then, the high frequency part of the $b_0$ data can be utilized as deficient data in a high frequency region to generate DWI data corresponding to b=$b_n$. When data is acquired by a PROPELLER method or a radial acquisition method, regridding processing that generates data on grid points in a Cartesian sampling from radial data by an interpolation processing is performed. The regridding processing and the composition processing of data can be separately performed in an arbitrary order but the regridding processing and the composition processing of data can be performed as a single processing.

In the regridding processing, a density function is generally used in order to perform data interpolation with weighting depending on a degree of data overlapping so that a weight becomes bigger when a data density is smaller while the weight becomes smaller when the data density is larger and equal density data can be generated from unequal density data by the density function. Then, image data can be obtained by performing FT on the equal density data.

Meanwhile, it is preferable to perform a weighting addition of the $b_0$ data and the $b_n$ data so that a weight for the $b_n$ data to be originally acquired becomes larger than that of the $b_0$ data in a low frequency part where the $b_0$ data overlaps with the $b_n$ data in data composition processing from the viewpoint of generating more adequate DWI data corresponding to $b_n$.

Moreover, in case of performing composition processing by a weighted interpolation of data, it is preferable to change the weight depending on a distance from a position of data to be obtained to original data from the viewpoint of generating more adequate DWI data. Specifically, composition processing of data can be performed in consideration of distances from the grid points to the respective pieces of data as well by determining the weights so that the weight becomes larger when a distance from a target grid point is shorter and the weight becomes smaller when the distance from the target grid point is longer.

Note that, the radial acquisition method is equivalent to the case where the blade width corresponds to 1 data line in the PROPELLER method. Therefore, in case of acquiring data by the radial acquisition method, it is only necessary to make each step angle of the $b_n$ data coarse with making each step angle of the $b_0$ data dense.

Further, composition processing of more than two pieces of data acquired in a Non Cartesian state as described above can be performed. Moreover, a Non Cartesian data acquisition method can be applied for generating pieces of image data corresponding to multiple parameters for controlling contrast other than the b-factor.

Moreover, in case of performing Non Cartesian sampling, overlapping data in a low frequency part can be used for a known motion correction. In this case, a shift between blades and a shift between the $b_0$ data and the $b_n$ data due to motions are to be corrected, and it is preferable to set reference data to a blade of the $b_0$ data that is not influenced by the motions. However, a blade of the $b_n$ data may be used as a reference.

3. Third Modification

When contrasts are mutually opposite between pieces of data subjected to composition processing, it is necessary to invert the sign of one or a part of the pieces of data before the composition processing to match magnitude relations of contrasts. However, the increasing and decreasing directions in contrast of the pieces of data are sometimes unknown. For that reason, the increasing and decreasing directions in contrast can be determined by using the pieces of data subjected to composition processing. This function can be provided with the data composition unit 43.

Figure 19:
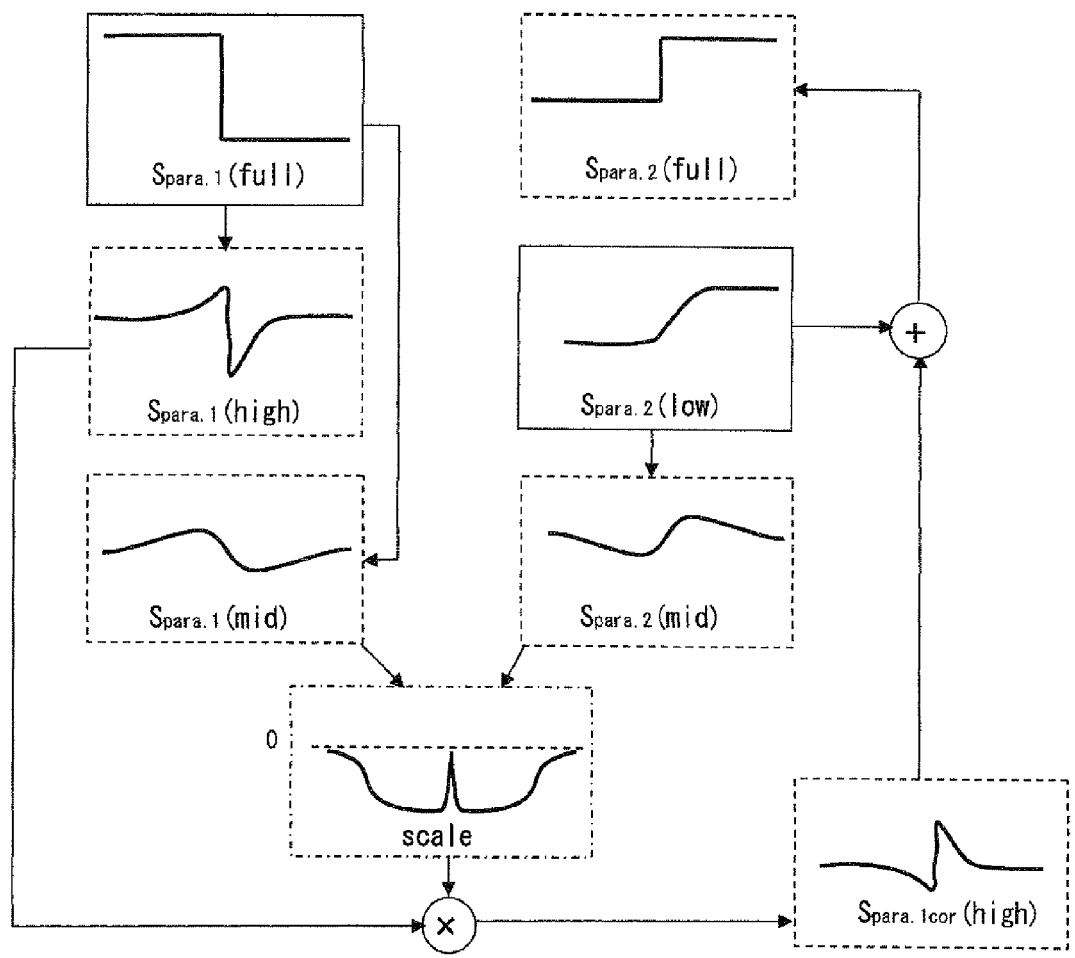
FIG. 19 is a flowchart explaining a method of performing composition processing with determining magnitude relation in contrast between pieces of data to be targets of the composition processing by calculating a ratio between pieces of data in an intermediate frequency region corresponding to a common part of the pieces of data to be targets of the composition processing to match increasing and decreasing direction in contrast with each other.

FIG. 19 is a flowchart explaining a method of performing composition processing with determining magnitude relation in contrast between pieces of data to be targets of the composition processing by calculating a ratio between pieces of data in an intermediate frequency region corresponding to a common part of the pieces of data to be targets of the composition processing to match increasing and decreasing direction in contrast with each other.

Each piece of data shown in FIG. 19 shows a profile of k-space data in a one-dimensional direction. That is, each ordinate denotes signal intensity S and each abscissa denotes position K in k-space.

As shown by the solid line frames in FIG. 19, a contrast of k-space data $S_{para.1}$ (full) corresponding to the first parameter value in the entire Frequency region and a contrast of k-space data $S_{para.2}$ (low) corresponding to the second parameter value in a low frequency region are sometimes mutually opposite. However, even if composing the k-space data $S_{para.1}$ (high) in a high frequency part extracted from the k-space data $S_{para.1}$ (full) having the inverted contrast corresponding to the first parameter value by a HPF (high pass filter) with the k-space data $S_{para.2}$ (low) corresponding to the second parameter value in the low frequency region as it is, the k-space data $S_{para.2}$ (full) with the contrast corresponding to the second parameter value in the entire frequency region can not be obtained.

For that reason, by extracting k-space data $S_{para.1}$ (mid) corresponding to the first parameter value and k-space data $S_{para.2}$ (mid) corresponding to the second parameter value in a middle frequency region corresponding to the overlapping region with MPFs (mid pass filters) and calculating a ratio thereof, a correction factor "scale" to correct each signal intensity can be determined together with the sign of the k-space data $S_{para.1}$ (high) with the inverted contrast. Note that, when an absolute value of the k-space data $S_{para.1}$ (mid) is not over a certain positive threshold Th, it is preferable to set the correction factor "scale" to zero since the corresponding part of the k-space data can be regarded as a no-signal part. Therefore, the correction factor "scale" can be determined as the formula (9).

$$\text{scale}=S_{para.2}(\text{mid})/S_{para.1}(\text{mid}):|S_{para.1}(\text{mid})|>Th=0: \text{otherwise} \quad (9)$$

Note that, the threshold Th is set to a value that can determine whether a signal is present, like several times a noise level.

Then, k-space data $S_{para.1.cor}$(high) with a corrected contrast in the high frequency region can be generated by multiplying the correction factor "scale" by the k-space data $S_{para.1}$ (high) corresponding to the first parameter value in the high frequency part as shown in the formula (10).

$$S_{para.1.cor}(\text{high})=\text{scale}*S_{para.1}(\text{high}) \quad (10)$$

Next, k-space data $S_{para.2}$ (full) corresponding to the second parameter value in the entire frequency region can be generated by adding the k-space data $S_{para.1.cor}$(high) with the corrected contrast in the high frequency region to the k-space data $S_{para.2}$(low) corresponding to the second parameter value in the low frequency region.

If a correction factor is determined by calculating a signal ratio in data in a common part between pieces of data subjected to composition processing by this means, increasing and decreasing directions of contrasts can be matched with each other since the correction factor becomes a negative value when a contrast inverts even in a case where the increasing and decreasing directions of contrasts are unknown. Therefore, it is effective in especially acquiring a T1WI and a T2WI having a high possibility that their contrasts become mutually opposite.

Meanwhile, in case of acquiring a PDWI and a T2WI having contrasts each showing a virtually similar tendency, omitting the foregoing processing sometimes leads to reduction of a data processing amount. Moreover, when it is known that the contrasts becomes mutually opposite, the magnitude relations of contrasts can be easily matched by simply inverting the sign of signal values of k-space data $S_{para.1}$ (high) corresponding to the first parameter value in a high frequency part. Specifically, the k-space data $S_{para.1}$(high) with the inverted sign in the high frequency part can be directly added to the k-space data $S_{para.2}$(low) in the low frequency region.

4. Other Modifications

Moreover, a density of data acquisition points for Cartesian state data acquisition as well as Non Cartesian state data acquisition can be changed per piece of k-space data to be subjected to composition processing. For example, if a density of data acquisition for a high frequency region having a less effect on a contrast is set to be rougher than that for a low frequency region, the number of data to be acquired can be reduced.

Further, the magnetic resonance imaging apparatus can be connected to an image processing apparatus through a network so that data composition processing can be performed in the image processing apparatus. In this case, the image processing apparatus is provided with functions to acquire k-space data or image data from the magnetic resonance imaging apparatus through the network, to perform correction processing and composition processing of the acquired k-space data or image data and to perform image reconstruction processing or IFT processing.

What is claimed is:

1. A magnetic resonance imaging apparatus comprising:
a data acquisition unit configured to acquire plural sets of magnetic resonance data for generating plural species of image data of an object having contrasts that are mutually different from each other, said sets of acquired data having mutually different data amounts respectively corresponding to parameter values for controlling respectively corresponding image contrasts to mutually different values; and
an image data generating unit configured to generate the plural species of the image data by performing both image reconstruction processing and composition processing of the plural sets of magnetic resonance data or of plural sets of data derived from the plural sets of magnetic resonance data,
wherein said data acquisition unit is configured to acquire the plural sets of magnetic resonance data wherein magnetic resonance data corresponding to at least one parameter value for controlling contrast has an amount of data necessary to generate image data and magnetic resonance data corresponding to at least one other parameter value for controlling contrast which has a data amount smaller than that necessary to generate image data.

2. A magnetic resonance imaging apparatus as in claim 1, wherein said data acquisition unit is configured to acquire the plural sets of magnetic resonance data so that magnetic resonance data corresponding to at least one other parameter value for controlling contrast are data only in a low frequency region.

3. A magnetic resonance imaging apparatus as in claim 1, wherein said data acquisition unit is configured to acquire the plural sets of magnetic resonance data for generating at least two of: (a) T1 weighted image data, (b) T2 weighted image data, (c) proton density image data, (d) fluid attenuated inversion recovery image data, (e) diffusion weighted image data, and (f) perfusion weighted image data.

4. A magnetic resonance imaging apparatus as in claim 1, wherein said data acquisition unit is configured to acquire one set of magnetic resonance data by setting a b value indicating an intensity of a motion probing gradient pulse to a first value which can be regarded as zero and acquire another set of magnetic resonance data by setting the b value to a second value larger than zero.

5. A magnetic resonance imaging apparatus as in claim 1, wherein said data acquisition unit is configured to acquire the plural sets of magnetic resonance data so that an application direction of a motion probing gradient pulse in acquisition of each set of magnetic resonance data is set to be a mutually different direction.

6. A magnetic resonance imaging apparatus as in claim 1, wherein said image data generating unit is configured to perform the composition processing after correcting amplitude and/or phase of the plural sets of magnetic resonance data or the sets of data.

7. A magnetic resonance imaging apparatus as in claim 1, wherein said image data generating unit is configured to perform the composition processing after correcting amplitude and/or phases of the plural sets of magnetic resonance data so that the amplitude and/or phase are matched between data having a maximum data amount and data having a non-maximum data amount.

8. A magnetic resonance imaging apparatus as in claim 1, wherein said image data generating unit is configured to perform the composition processing after correcting amplitude and/or phases of plural sets of real space data derived from the plural sets of magnetic resonance data without changing the data format from a complex data format.

9. A magnetic resonance imaging apparatus as in claim 1, wherein said data acquisition unit is configured to acquire the plural sets of magnetic resonance data so that the plural sets of magnetic resonance data subjected to the composition processing or the plural sets of data subjected to the composition processing overlap between each set, and
said image data generating unit is configured to perform the composition processing after performing correction processing of the plural sets of magnetic resonance data or the plural sets of data by using a correction parameter obtained based on data from a part where the plural sets of magnetic resonance data or the plural sets of the data overlap between each set.

10. A magnetic resonance imaging apparatus as in claim 1, wherein said data acquisition unit is configured to acquire the plural sets of magnetic resonance data so that the plural sets of magnetic resonance data subjected to the composition processing or the plural sets of data subjected to the composition processing overlap between each set, and
said image data generating unit is configured to perform the composition processing after performing windowing of the plural sets of magnetic resonance data or the plural sets of data by using weighting functions.

11. A magnetic resonance imaging apparatus as in claim 1, wherein said data acquisition unit is configured to acquire magnetic resonance data corresponding to the first value by single shot data acquisition and to acquire magnetic resonance data corresponding to the second value by multi-shot data acquisition.

12. A magnetic resonance imaging apparatus as in claim 1, wherein said data acquisition unit is configured to acquire magnetic resonance data corresponding to the first value by single shot data acquisition and to acquire magnetic resonance data corresponding to the second value by multi-shot data acquisition.

13. A magnetic resonance imaging apparatus as in claim 1, wherein said data acquisition unit is configured to acquire plural sets of magnetic resonance data for generating plural species of image data each having arbitrary spatial axes and a time axis.

14. A magnetic resonance imaging apparatus as in claim 1, wherein said data acquisition unit is configured to acquire the plural sets of magnetic resonance data by setting b values each indicating an intensity of a motion probing gradient pulse to mutually different values, and said image data generating unit is configured to generate one of the plural species of image data based on k-space data arranged from a center part of k-space toward a high frequency side in a descending order of amplitude of a corresponding b value by respectively performing composition processing of the plural sets of magnetic resonance data corresponding to the mutually different b values.

15. A magnetic resonance imaging apparatus as in claim 1, wherein said data acquisition unit is configured to acquire plural sets of magnetic resonance data corresponding to motion probing gradient pulses of which application directions are set to mutually different directions including an isotropic direction, and
said image data generating unit is configured to generate one of the plural species of image data based on k-space data in which magnetic resonance data acquired by applying a motion probing gradient pulse in the isotropic direction are arranged in a center part of k-space.

16. A magnetic resonance imaging apparatus as in claim 1, wherein said data acquisition unit is configured to set a same parameter for respectively controlling contrast in acquisition of at least three sets of magnetic resonance data to mutually different values per set.

17. A magnetic resonance imaging apparatus as in claim 1, wherein said data acquisition unit is configured to set plural scans for acquisition of the plural sets of magnetic resonance data in one data acquisition sequence and to set parameters for controlling contrast in the acquisition so that each of the parameters includes at least three values and the values of each parameter are mutually different per scan.

18. A magnetic resonance imaging apparatus as in claim 1, wherein said image data generating unit is configured to generate one of the plural species of image data based on k-space data obtained by arranging the plural sets of magnetic resonance data in k-space from a low frequency side toward a high frequency side of k-space in an order of similarity degree of contrast of image data obtained from each set of magnetic resonance data to a desired contrast.

19. A magnetic resonance imaging apparatus as in claim 1, wherein said data acquisition unit is configured to acquire the plural sets of magnetic resonance data in a non-orthogonal manner.

20. A magnetic resonance imaging apparatus as in claim 1, wherein said image data generating unit is configured to perform the composition processing by matching magnitude relation of contrast of the plural sets of magnetic resonance data or the plural sets of data.

21. A magnetic resonance imaging apparatus as in claim 20, wherein said image data generating unit is configured to match the magnitude relation of contrast by inverting a sign of data having an inverse contrast out of the plural sets of magnetic resonance data or the plural sets of data.

22. A magnetic resonance imaging apparatus as in claim 20, wherein said image data generating unit is configured to determine the magnitude relation of contrast by calculating a ratio between sets of data corresponding to a common part of the plural sets of magnetic resonance data or the plural sets of data and match the determined magnitude relation of contrast.

23. The magnetic resonance imaging apparatus as in claim 1, wherein said image data generating unit is configured to perform the composition processing, after correcting amplitude and/or phases of the plural sets of data so that amplitude and/or phases are matched between data derived from magnetic resonance data whose data amount is maximum and other data derived from magnetic resonance data whose data amounts are not maximum.

24. A magnetic resonance imaging method comprising:
acquiring plural sets of magnetic resonance data for generating plural species of image data of an object having contrasts that are mutually different from each other, said sets of acquired data having mutually different data amounts respectively corresponding to parameter values for controlling respectively corresponding image contrasts to mutually different values; and
generating the plural species of the image data by performing image reconstruction processing and composition processing of the plural sets of magnetic resonance data or of plural sets of data derived from the plural sets of magnetic resonance data,
wherein said plural sets of magnetic resonance data are acquired corresponding to at least one parameter value for controlling contrast have an amount of data necessary to generate image data and magnetic resonance data corresponding to at least one other parameter value for controlling contrast which has a data amount smaller than that necessary to generate image data.

* * * * *